US010822589B2

(12) United States Patent
Spanholtz et al.

(10) Patent No.: US 10,822,589 B2
(45) Date of Patent: Nov. 3, 2020

(54) EX VIVO NK CELL DIFFERENTIATION FROM CD34+ HEMATOPOIETIC CELLS

(71) Applicant: IPD-Therapeutics B.V., Oss (NL)

(72) Inventors: Jan Spanholtz, Kleve (DE); Harmen Dolstra, Nijmegen (NL)

(73) Assignee: GLYCOSTEM THERAPEUTICS B.V., Oss (NL)

(*) Notice: Subject to any disclaimer, the term of this patent is extended or adjusted under 35 U.S.C. 154(b) by 0 days.

(21) Appl. No.: 15/711,141

(22) Filed: Sep. 21, 2017

(65) Prior Publication Data

US 2018/0044636 A1 Feb. 15, 2018

Related U.S. Application Data

(62) Division of application No. 14/376,870, filed as application No. PCT/NL2013/050037 on Feb. 7, 2013, now abandoned.

(30) Foreign Application Priority Data

Feb. 8, 2012 (EP) ..................... 12154554

(51) Int. Cl.
C12N 5/02 (2006.01)
C12N 5/0783 (2010.01)
A61K 35/17 (2015.01)
A61K 39/395 (2006.01)

(52) U.S. Cl.
CPC ............ *C12N 5/0646* (2013.01); *A61K 35/17* (2013.01); *A61K 39/39558* (2013.01); *C12N 2501/125* (2013.01); *C12N 2501/145* (2013.01); *C12N 2501/21* (2013.01); *C12N 2501/22* (2013.01); *C12N 2501/2302* (2013.01); *C12N 2501/2306* (2013.01); *C12N 2501/2307* (2013.01); *C12N 2501/2312* (2013.01); *C12N 2501/2315* (2013.01); *C12N 2501/26* (2013.01); *C12N 2501/91* (2013.01)

(58) Field of Classification Search
None
See application file for complete search history.

(56) References Cited

U.S. PATENT DOCUMENTS 9,109,202 B2 * 8/2015 Spanholtz ............ C12N 5/0607
9,193,953 B2 * 11/2015 Spanholtz ............ C12N 5/0646

FOREIGN PATENT DOCUMENTS

| WO | 2006004592 A2 | | 1/2006 |
|---|---|---|---|
| WO | WO 2006004592 | * | 1/2006 |
| WO | 2006102209 A2 | | 9/2006 |
| WO | 2007037682 A1 | | 4/2007 |

OTHER PUBLICATIONS

Blomberg et al, "Europium-labelled target cells in an assay of natural killer cell activity. I. A novel non-radioactive method based on time-resolved fluorescence," Journal of Immunology Methods, vol. 86, pp. 225-229, 1986.
Wojta et al, "Vascular origin determines plasminogen activator expression in human endothelial cells. Renal endothelial cells produce large amounts of single chain urokinase type plasminogen activator," Journal of Biological Chemistry, vol. 264, pp. 2846-2852,1989.
Trinchieri et al, "Immunoregulation by interleukin-12," Journal Leukocyte Biology, vol. 59, pp. 505-511, 1996.
Bennett et al, "Definition of a natural killer NKR-P1A-+/CD56-/CD16-functionally immature human NK cell subset that differentiates in vitro in the presence of interleukin 12," J. Exp. Med., vol. 184, pp. 1845-1856, 1996.
McDyer et al, "The regulation of IL-12: its role in infectious, autoimmune, and allergic diseases," J Allergy Clin Immunol, vol. 102, pp. 11-15, 1998.
Galon et al, "IL-12 induces IFN regulating factor-1 (IRF-1) gene expression in human NK and T cells," Journal of Immunology, vol. 162, pp. 7256-7262, 1999.
Cooper et al, "Human natural killer cells: a unique innate immunoregulatory role for the CD56(bright) subset," Blood, vol. 97, pp. 3146-3151, 2001.
Irjala et al, "Mannose receptor is a novel ligand for L-selectin and mediates lymphocyte binding to lymphatic endothelium," J. Exp. Med., vol. 194, pp. 1033-1042, 2001.
Cooper et al, "The biology of human natural killer-cell subsets," Trends in Immunology, vol. 22, pp. 633-640, 2001.
Yamamoto et al, "The human perforin gene is a direct target of STAT4 activated by IL-12 in NK cells," Biochemical and Biophysical Research Commununications, vol. 297, pp. 1245-1252, 2002.

(Continued)

Primary Examiner — Michail A Belyavskyi
(74) Attorney, Agent, or Firm — Hoffmann & Baron, LLP

(57) ABSTRACT

The present invention relates to the ex vivo differentiation of NK cells from CD34+ hematopoietic stem cells. Such NK cells and their progenitor cells can be used in therapies of a broad range of malignancies. In the present invention it is shown that IL-12 modulates ex vivo NK cell differentiation. Specific, we achieved significantly higher expression of KIR, CD16 and CD62L in the presence of IL-12 in the cell culture system. The induction of receptor expression by IL-12 occurred predominantly on an augmented population of CD33+NKG2A+ NK cells early during NK cell differentiation. These cells further show enhanced cytolytic activity against MHC class I positive AML targets. In line with the enhanced CD16 expression, IL-12 modulated ex vivo generated NK cells exhibit an improved antibody-dependent-cytotoxicity, using anti CD20 antibody on various B cell targets. Additional to the enhanced expression of CD62L, we show that this cell population consists of a specific chemokine receptor profile. By showing an increased capacity for adhesion to lymphendothelial cells and a specific chemokine receptor profile, we show that IL-12 provided the ex vivo generated NK cells with specific tissue-homing abilities.

5 Claims, 12 Drawing Sheets

(56) References Cited

OTHER PUBLICATIONS

Robertson et al, "Role of chemokines in the biology of natural killer cells," Journal of Leukocyte Biology, vol. 71, pp. 173-183, 2002.
Loza et al, "The IL-12 signature: NK cell terminal CD56+high stage and effector functions," Journal of Immunology, vol. 172, pp. 88-96, 2004.
Alter et al, "CD107a as a functional marker for the identification of natural killer cell activity," Journal Immunological Methods, vol. 294, pp. 15-22, 2004.
Zhang et al, "Murine hematopoietic stem cells change their surface phenotype during ex vivo expansion," Blood, vol. 105, pp. 4314-4320, 2005.
Berahovich et al, "Evidence for NK cell subsets based on chemokine receptor expression," Journal of Immunology, vol. 177, pp. 7833-7840, 2006.
Romagnani et al, "CD56brightCD16- killer Ig-like receptor—NK cells display longer telomeres and acquire features of CD56dim NK cells upon activation," Journal of Immunology, vol. 178, pp. 4947-4955, 2007.
Takahashi et al, "Induction of CD16+ CD56bright NK cells with antitumour cytotoxicity not only from CD16-CD56bright NK Cells but also from CD16-CD56dim NK cells," Scandinavian Journal of Immunology, vol. 65, pp. 126-138, 2007.
Bhat et al, "Serial killing of tumor cells by human natural killer cells-enhancement by therapeutic antibodies," PLoS One 2, Issue 3, vol. e326, 2007.
Ljunggren et al, "Prospects for the use of NK cells in immunotherapy of human cancer," Nature Reviews Immunology, vol. 7, pp. 329-339, 2007.
Binyamin et al, "Blocking NK cell inhibitory self-recognition promotes antibody-dependent cellular cytotoxicity in a model of anti-lymphoma therapy," Journal of Immunology, vol. 180, pp. 6392-6401, 2008.
Guia et al, "A role for interleukin-12/23 in the maturation of human natural killer and CD56+ T cells in vivo," Blood, vol. 111, pp. 5008-5016, 2008.
Di Santo, "Natural killer cells: diversity in search of a niche," Nature Immunology, vol. 9, pp. 473-475, 2008.
Spanholtz et al, "Preclinical ex-vivo generation of clinical relevant amounts of NK cells from CD34+ progenitor cells for immunotherapy," Blood ASH Annual Meeting Abstracts, vol. 112, Abstract 2916, 2008.
Marttila-Ichihara et al, "Macrophage mannose receptor on lymphatics controls cell trafficking," Blood, vol. 112, pp. 64-72, 2008.
Saez-Borderias et al, "IL-12-dependent inducible expression of the CD94/NKG2A inhibitory receptor regulates CD94/NKG2C+ NK cell function," Journal of Immunology, vol. 182, pp. 829-836, 2009.
Sutlu et al, "Natural killer cell-based immunotherapy in cancer: current insights and future prospects," Journal of Internal Medicine, vol. 266, pp. 154-181, 2009.
Spanholtz et al, "Clinical scale generation of functional human natural killer cells from umbilical cord blood CD34-positive cells for immunotherapy," Blood ASH Annual Meeting Abstracts, vol. 114, Abstract 2666, 2009.
Costa et al, "IFN-α-mediated increase in cytolytic activity of maturing NK cell upon exposure to HSF-invected myelomonocytes," Eur. Journal of Immunology, vol. 39, pp. 147-158, 2009.
Delaney et al, "Notch-mediated expansion of human cord blood progenitor cells capable of rapid myeloid reconstitution," Nature Meddicine, vol. 16, pp. 232-236, 2010.
Spanholtz et al, "High log-scale expansion of functional human natural killer cells from umbilical cord blood CD34-positive cells for adoptive cancer immunotherapy," PLoS One vol. 5, Issue 2, e9221, 2010.
Doulatov et al, "Revised map of the human progenitor hierarchy shows the origin of macrophages and dendritic cells in early lymphoid development," Nature Immunology, vol. 11, pp. 585-593, 2010.
Juelke et al, "CD62L expression identifies a unique subset of polyfunctional CD56dim NK cells," Blood, vol. 116, pp. 1299-1307, 2010.
Moretta, "Dissecting CD56dim human NK cells," Blood vol. 116, pp. 3689-3691, 2010.
Boitano et al, "Aryl hydrocarbon receptor antagonists promote the expansion of human hematopoietic stem cells," Science, vol. 329, pp. 1345-1348, 2010.
Moroso et al, "NK cells can generate from precursors in the adult human liver," European Journal of Immunology, vol. 41, pp. 3340-3350, 2011.
Grzywacz et al, "Natural killer-cell differentiation by myeloid progenitors," Blood, vol. 117, pp. 3548-3558, 2011.
Vacca et al, "CD34+ hematopoietic precursors are present in human decidua and differentiate into natural killer cells upon interaction with stromal cells," Proc Natl Acad Sci U S A, vol. 108, pp. 2402-2407, 2011.
Spanholtz et al, "Clinical-grade generation of active NK cells from cord blood hematopoietic progenitor cells for immunotherapy using a closed-system culture process," PLoS One, vol. 6, Issue 6, e20740, 2011.
Beziat et al, "CD56brightCD16+ NK cells: a functional intermediate stage of NK cell differentiation," Journal of Immunology, vol. 186, pp. 6753-6761, 2011.
Eissens et al, "Defining Early Human NK Cell Developmental Stages in Primary and Secondary Lymphoid Tissues" PLoS One vol. 7, Issue 2, e30930, 2012.
Zhang et al, "Insulin-like growth factor 2 expressed in a novel fetal liver cell population is a growth factor for hematopoietic stem cells," Blood vol. 103, pp. 2513-2521, 2004.
Yu et al., "Enhancement of Human Cord Blood CD34+ Cell-Derived NK Cell Cytotoxicity by Dendritic Cells", Journal of Immunology, vol. 166, pp. 1590-1600, 2001.
Barao et al., "IL-15-Mediated Induction of LFA-1 is a Late Step Required for Cytotoxic Differentiation of Human NK Cells from CD34+Lin-Bone Marrow Cells", Journal of Immunology, vol. 171, pp. 683-690, 2003.

\* cited by examiner

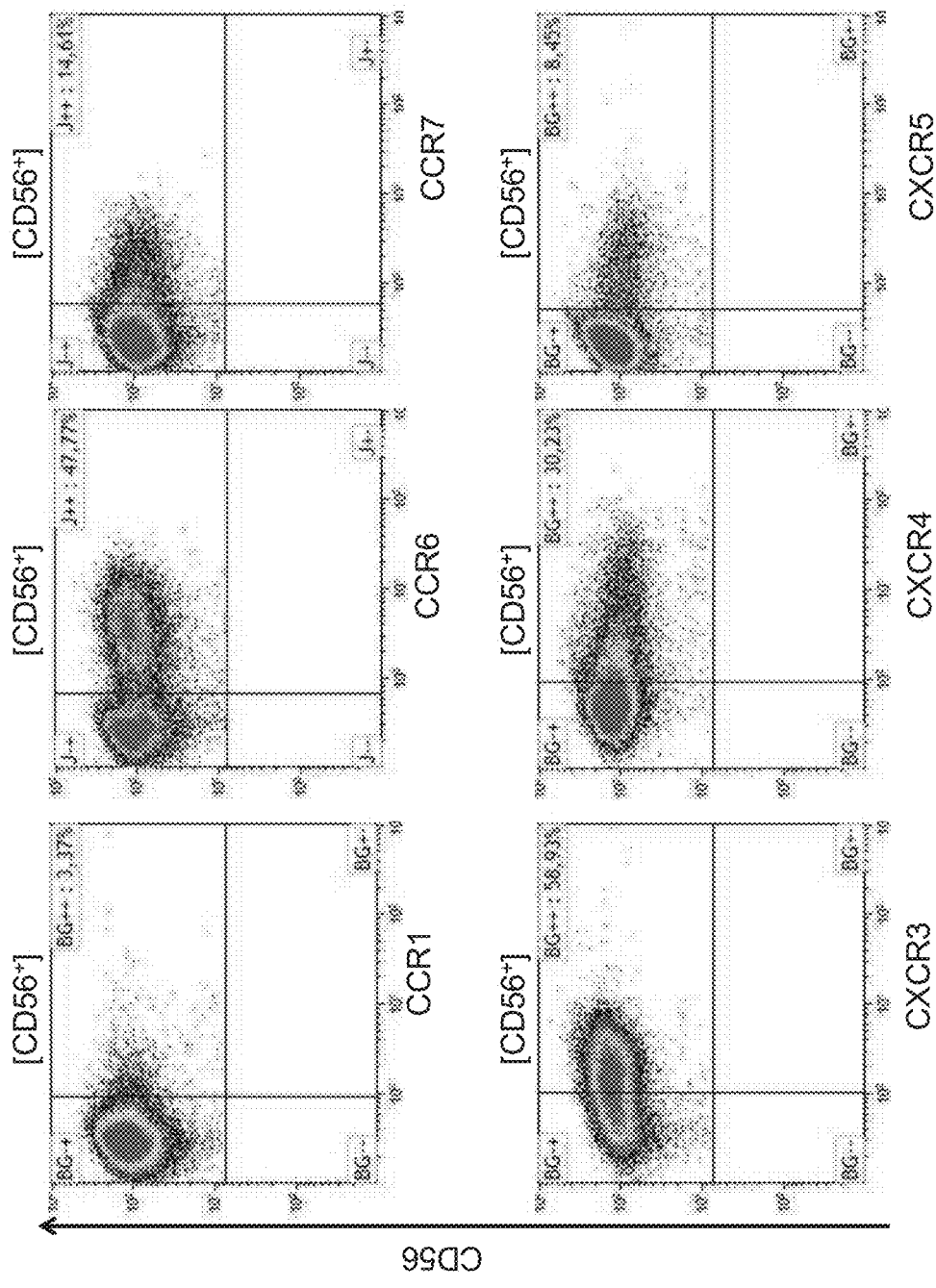

A

B

*p< 0.05

EX VIVO NK CELL DIFFERENTIATION FROM CD34+ HEMATOPOIETIC CELLS

This application is a divisional of U.S. application Ser. No. 14/376,870 filed Aug. 6, 2014, which has been abandoned, and was the U.S. National Phase of, and Applicants claim priority from, International Application No. PCT/NL2012/050132 filed Mar. 5, 2012, which claims priority from European Application No. EP 11157001.6, each of which is incorporated herein by reference.

BACKGROUND OF THE INVENTION

The invention relates to the field of modern medical biology. In particular the invention relates to stem cell technology. More in particular the invention relates to the ex vivo generation of NK cells from such cells. The NK cells can, for instance be used in the treatment of cancer and chronic infectious disease. The invention also relates to particular postembryonic and or adult stem cell technology and the generation of NK cells from cultures of such cells.

Natural Killer (NK) cells are innate lymphocytes that exhibit cytotoxic and immunoregulatory functions upon activation. Generally these functions are correlated with two distinct NK cell CD56 positive phenotypes, namely the cytokine producing $CD56^{bright}$ NK cells that are most prominently found in secondary lymphoid tissues and the blood resident $CD56^{dim}$ NK cells exerting killing of virus-infected and transformed cells[1-3]. Both NK cell subtypes express a typical range of activating and inhibiting receptors balancing their activity. $CD56^{dim}$ NK cells are found to exhibit high surface expression of KIR and CD16 (FcRγIII), the receptor mediating antibody-dependent cytotoxicity (ADCC), whereas $CD56^{bright}$ NK cells lack the expression of these receptors but reveal more intensive expression of i.e. the inhibitory receptor CD94/NKG2A. Several indications led to the concept of a stepwise maturation of $CD56^{bright}$ NK cells towards a $CD56^{dim}$ phenotype and function of NK cells[2,4,5]. Furthermore, related to the homing sites of these two NK cell subsets a differing expression of chemokine receptor and adhesion molecules was identified. Whereas $CD56^{bright}$ NK cells exclusively express CCR7 and exhibit higher levels of i.e. CD62L, CCR1 and CCR4, 5, 6, 7, 8 and 9 than $CD56^{dim}$ NK cells, other receptors such CCR4 and CXCR1, 2, 3 and 4 as well as CX3CR1 exhibit stronger expression on $CD56^{dim}$ NK cells [2,6,7].

Several cytokines exhibit significant biological effects on NK cells. Among those, IL-12, which is mainly produced by activated monocytes, macrophages, dendritic cells and B-cells, was shown to induce proliferation of NK cells, production of cytokines such as IFN-γ and to enhance cytotoxicity[8,9]. In addition, it has been demonstrated, that IL-12 also influences the receptor expression of NK cells. Early studies revealed an induction of the $CD56^{bright}$ NK cell phenotype by IL-12, including an up regulation of CD94 and CD62L and a down modulation of CD16[10]. Recently, an up regulation of NKG2A on NKG2C+ NK cells was shown as well [11].

NK cells have been described as promising effectors for adoptive immunotherapy of cancer[12,13]. We recently established and characterized an ex vivo human NK cell differentiation system, that provides an auspicious NK cell product for clinical therapies especially due to the availability, purity, high expansion rates and activation state of the generated NK cells alongside with their cytotoxic activity[14,15].

DESCRIPTION OF THE INVENTION

In the present invention we show that IL-12 affects the differentiation, receptor expression and function of ex vivo generated NK cells, in particular of NK cells that are generated from hematopoietic stem cells and hematopoietic progenitor cells cultured ex vivo. We found that IL-12 induces expression of CD62L, CD16 and KIR and a specific chemokine receptor repertoire alongside with correlated improved functions and capacities in cytotoxicity, ADCC and migration of the ex vivo differentiated human NK cells. The use of IL-12, preferably already at a stage wherein the culture does not contain detectable amounts of NK cells provides the finished NK cell product with new and/or enhanced properties.

To this end the invention provides a method for producing NK cells said method comprising
  i—providing a sample of human CD34 positive cells,
  ii—expanding said CD34 positive cells ex vivo,
  iii—culturing CD34 positive cells obtained in step ii ex vivo in an NK-cell differentiation medium,
  said method characterized in that said NK-differentiation medium comprises IL-12.

The invention further provides a method for producing NK cells said method comprising
  i—providing a sample of stem cells, progenitor cells or both, from human postembryonic tissue cells,
  ii—culturing and expanding said cells ex vivo,
  iii—culturing stem cells, progenitors or both obtained in step ii ex vivo in an NK-cell differentiation medium,
  said method characterized in that said NK-differentiation medium comprises IL-12.

Human hematopoietic stem cells and progenitor cells typically express the CD34 cell surface marker. Sources of hematopoietic stem and progenitor cells such as bone marrow, mobilized peripheral blood hematopoietic or cord blood are often treated with affinity purification using an antibody specific for human CD34 to enrich for such cells.

The CD34 positive cell, hematopoietic stem cell or progenitor cell can be derived from the blood, from the bone marrow or from another source of postnatal hematopoietic progenitor cells. In a preferred embodiment the CD34 positive cell, hematopoietic stem cell or progenitor cell is derived from human postembryonic tissue. Preferably the sample containing the human CD34 positive cells, hematopoietic stem cells or progenitor cells is a cell population that is enriched for CD34 positive cells, preferably by means of affinity purification using an anti-CD34 antibody. Example sources of hematopoietic stem cells and/or progenitor cells that are suited for use in a method of the invention are: bone marrow, mobilized peripheral blood, adult fat tissue (mesenchymal stem cells), the blood of a new born infant, preferably from blood collected from the umbilical cord or placenta, after disconnecting it from the new-born. Presently hematopoietic stem cells and hematopoietic progenitor cells can be obtained from stem cell lines that have been generated previously. Presently it is possible to reprogram tissue specific stem cells such as skin stem cells to produce committed progenitors cells in the hematopoietic lineage. It has even been shown to be possible to reprogram differentiated cells, such as skin cells, into fully functional stem cells that can produce progeny of progenitor cells that are committed to producing differentiated progeny of the hematopoietic lineage. All of such stem cells are suitable hematopoietic stem cells for the present invention. A preferred source of hematopoietic stem cells is hematopoietic and/or mesenchymal human post-embryonic tissue.

Preferably from human tissue obtained from postpartum humans. A particularly preferred source is human cord blood. In a particularly preferred embodiment, said source, is a source of frozen human cord blood. Thus in a particularly preferred embodiment the CD34 positive cell, hematopoietic stem cell or progenitor cell is a CD34 positive cell, hematopoietic stem cell or progenitor cell is derived from human cord blood. In a preferred embodiment said sample comprises a human cord blood sample. In a preferred embodiment said CD34 positive cells are CD34 positive cells from the cord blood of a human. A hematopoietic progenitor cell typically does not express an NK cell marker.

A hematopoietic stem cell is defined by its ability to replenish all blood cell types and their ability to self-renew. It is known that a small number of hematopoietic stem cells can expand to generate a very large number of daughter hematopoietic stem cells. A hematopoietic progenitor cell is a cell that, like a stem cell, has a tendency to differentiate into a specific type of cell, but is already more specific than a stem cell and is pushed to differentiate into its "target" cell. A difference between stem cells and progenitor cells is that stem cells can replicate (self-renew) indefinitely, whereas progenitor cells can only divide a limited number of times. Another difference is the expression of surface markers. Stem cells typically lack surface markers that are prominent on the progenitor cells or differentiated cells derived from them. However, in humans both hematopoietic stem cells and hematopoietic progenitor cells express the cell surface marker CD34.

Earlier studies indicated the potency of IL-12 to modulate the maturation towards a cytotoxic and IFN-γ producing NK cell[16]. The term maturation is typically used for the change of an immature NK-cell into a more mature form. In the art this is sometimes also referred to as differentiation, however, for the present invention the term differentiation is used to reflect production of a cell expressing a typical NK-cell marker, from a precursor cell that does not express a typical NK-cell marker. In recent years, patients with dysfunctions in IL-12-signaling pathways revealed the necessity of NK cell priming through IL-12 for the acquisition of functional activity[17]. The acquisition of cytotoxic and IFN-γ producing NK cell functions by IL-12 was correlated with induced expression of the IFN regulating factor-1 (IRF-1) and perforin genes[18, 19]. In the present invention it was found that IL-12 already has a function when added to a culture that comprises hematopoietic stem and/or progenitor cells. Without being bound by theory it is believed that IL-12 is not only effective on mature and immature NK-cells but also on precursor cells thereof that do not express a typical NK-cell marker like CD56, NKG2A, KIR or NKp46.

The culture is typically started with an expansion step. In this step the number of CD34 positive cells, hematopoietic stem cells, hematopoietic progenitor cells, or a combination thereof, is increased. Presently, a number of different methods are available for expanding CD34 positive cells, hematopoietic stem cells, hematopoietic progenitor cells, or a combination thereof. Such methods include but are not limited to culture in the presence of SCF (Stem cell factor), TPO (Thrombopoietin), IGF-2 (Insulin—like growth factor-2), FGF-1 (Fibroblast growth factor-1), Angptl-2 (Angiopoietin-like protein 2); culture in the presence of SCF, TPO; culture in the presence of SCF, flt-3Ligand (FLT-3L), Interleukin 6 (IL-6) and IGF-2; and culture in the presence of SCF, TPO and IGF-2[20, 21]. Additional clinically applicable CD34+ expansion methods used the combinations of SCF, TPO, FLT-3L, Interleukin 3 (IL-3), IL-6 in combination with immobilized Notch ligand (Delta1$^{ext-IgG}$)[22] or small synthetic compounds like the family of aryl hydrocarbon receptor antagonists, such as but not limited to StemRegenin 1 (SR1) in combination with SCF. TPO, FLT-3L and IL-6[23].

Step ii of a method of the invention is preferably performed in a culture medium comprising three or more of stem cell factor (SCF), flt-3Ligand (FLT-3L), thrombopoietin (TPO) and interleukin-7 (IL-7) and three or more of granulocyte-macrophage-colony-stimulating factor (GM-CSF), granulocyte-colony-stimulating factor (G-CSF), interleukin-6 (IL-6), leukaemia-inhibitory factor (LIF) and Macrophage-inflammatory protein-1alpha (MIP-1 alpha). In a particularly preferred embodiment step ii is performed in a culture medium comprising stem cell factor (SCF), flt-3Ligand (FLT-3L), thrombopoietin (TPO) and interleukin-7 (IL-7); and granulocyte-macrophage-colony-stimulating factor (GM-CSF), granulocyte-colony-stimulating factor (G-CSF), interleukin-6 (IL-6). In a preferred embodiment said culture medium further comprises LIF and MIP-1 alpha. The amounts of cytokine added are conventional in the art, preferred amounts are given in the examples, but 10% deviations in amount are very well acceptable and within the scope of the present invention. Typical amounts for cytokines are TPO; 25 ng/ml; FLT-3L; 25 ng/ml, SCF; 25 ng/ml and IL-7; 25 ng/ml. For the GM-CSF, G-CSF, IL-6, LIF and MIP-1 alpha a low amount is given, typical amounts are GM-CSF; 10 pg/ml, G-CSF; 250 pg/ml, LIF; 50 pg/ml, MIP-1 alpha; 200 pg/ml and IL-6; 50 pg/ml.

Step ii is preferably performed in a culture medium comprising heparin, preferably low molecular weight heparins (LMHWs). LMWHs are used in the clinic, for instance as an anti-coagulant in diseases that feature thrombosis or prophylaxis of thrombosis. The LMWHs, are short chains of polysaccharide. LMWHs are defined as heparin or heparin salts having an average molecular weight of between about 2000-10000 Dalton, preferably between 5000 and 8000 Dalton and more preferably about 8000 Dalton, with preferably at least 60% of the chains being less than the average chain length. When the low molecular weight heparin average about 8000 Dalton it is preferred that at least 60% of all chains have a molecular weight less than 8000 Dalton. LMWHs can be obtained by various methods of fractionation or depolymerisation of polymeric heparin. Various methods of heparin depolymerisation are used in the manufacture of low molecular weight heparin. A non-limiting list is given herein below. A heparin of the invention can obtained from a mammal or other organism such as snails, alternatively heparins are synthesized synthetically or semi-synthetically. An example of the latter is production of heparin in bacteria such as but not limited to the heparin K5 by E. coli. Modifications of heparin such but not limited to acytylation, desulphatation and phosphorylation are also considered to be a heparin as defined in this invention. Non-limiting but preferred examples of such modifications are completely or partially desulfated LMWH, completely or partially desulfated and completely or partially Re-N-acetylated LMWH, completely or partially desulfated and completely or partially Re-N-sulfated LMWH, Substance L4 or completely or partially desulfated and completely or partially Re-N-phosphorylated LMWH. Preferred are LMWH preparations wherein at least 60% of all chains have a molecular weight less than 8000 Da. These can be obtained by various methods of fractionation or depolymerisation of polymeric heparin. Various methods of heparin depolymerisation are used in the manufacture of low molecular weight heparin. A non-limiting list is given herein below.

The LMWH for use in the present invention is preferably derived from standard heparin by UFH-depolymerization.

Oxidative depolymerisation with hydrogen peroxide is used in the manufacture of ardeparin (Normiflo®). Deaminative cleavage with isoamyl nitrite is used in the manufacture of certoparin (Sandoparin®). Alkaline beta-eliminative cleavage of the benzyl ester of heparin is used in the manufacture of enoxaparin (Lovenox® and Clexane®). Oxidative depolymerisation with Cu2+ and hydrogen peroxide is used in the manufacture of parnaparin (Fluxum®). Beta-eliminative cleavage by the heparinase enzyme is, used in the manufacture of tinzaparin (Innohep® and Logiparin®). Deaminative cleavage with nitrous acid is used in the manufacture of dalteparin (Fragmin®), reviparin (Clivarin®) and nadroparin (Fraxiparin®). When present in a culture medium it preferably comprises about 1-100, more preferably about 15-50 mg/l of LMWH.

The expansion of CD34 positive cells, hematopoietic stem cells, hematopoietic progenitor cells, or a combination thereof, can be determined with a number of different tests for the presence of CD34 positive cells, hematopoietic stem cells or hematopoietic progenitor cells. Such tests include tests for the presence of myeloid and/or lymphoid colony formation in vitro and test that measure repopulation of hematopoietic lineages in NOD-SCID mice supporting flowcytometric analyzes[24].

The expansion step ii is preferably performed for a period of at least 4 days. More preferably for at least 5 days, most preferably for at least 6, 7, 8 or 9 days and in particular at least 10 days.

The CD34 positive cells, hematopoietic stem cells, hematopoietic progenitor cells, or a combination thereof obtained in step ii, are in a next step iii cultured in an NK-cell differentiation medium. The NK cells can be obtained by culturing the cells obtained in step ii, in a medium comprising IL-3 (5 ng/mL), IL-7 (20 ng/mL), IL-15 (10 ng/mL), SCF (20 ng/mL), and FLT-3L (10 ng/mL)[25] or SCF, Flt3-L, IL-7, IL-15, IL-21 and GM-CSF 20 ng/ml each [26] in combination with stromal cells or stem cell factor (SCF) (20 ng/mL), FMS-like tyrosine kinase (FLT3-L) (20 ng/mL), interleukin-7 (IL-7) (20 ng/mL), IL-15 (20 ng/mL) and IL-21 (20 ng/mL)[27]. In the context of the invention, the above NK-differentiation media are provided with the proviso that they further comprise IL-12.

In a preferred embodiment of the invention step iii) is performed with an NK-cell differentiation medium that apart from IL-12 further comprises one or more of IL-2 and IL-15; and one or more of IL-7 and SCF; and three or more GM-CSF, G-CSF, IL-6, LIF and MIP-I alpha. In another preferred embodiment the NK-cell differentiation medium that comprises IL-12 further comprises one or more of SCF, IL-2, IL-7 and IL-15 and three or more of GM-CSF, G-CSF, IL-6, LIF and MIP-1 alpha. In a particularly preferred embodiment the NK-cell differentiation medium comprises apart from IL-12, the factors SCF, IL-2, IL-7, IL-15, GM-CSF, G-CSF, IL-6, LIF and MIP-1 alpha. In a preferred embodiment said NK-cell differentiation medium comprises 11-15, SCF and IL-12 and one or more of IL-2 and IL-7 and three or more GM-CSF, G-CSF, IL-6, LIF and MIP-1 alpha.

As for step iii, the amounts of the cytokine mentioned here that are added to the medium to from the NK-cell differentiation medium are conventional in the art, preferred amounts are given in the examples, but 10% deviations in amount are very well acceptable and within the scope of the present invention. For IL-15 and IL-2 the amounts are typically as follows: IL-15 (20 ng/ml), IL-2 (Proleukin© [Chiron]; 1000U/ml). A culture medium is an NK-cell differentiation medium if it contains at least IL15 or IL-2.

Part of step iii can be performed in a culture medium that comprises LMWH. However, this step is often performed in the absence of LMWH. When LMWH is included in the NK cell differentiation medium, it is preferred that it is included only in the first days of step iii, preferably in the first 4 days of culturing in step iii. The culturing step of step iii is preferably performed for at least 7 days, preferably at least 8, 9, 10, 11, 12, 13 days. In a particularly preferred embodiment the culturing step of step iii is performed for at least 14 days.

The method for producing NK cells as claimed in the present invention is characterised in that the NK-cell differentiation medium comprises interleukin-12 (IL-12). In a preferred embodiment said NK-differentiation medium comprises between 20 pgram/ml and 20 ngram/ml IL-12. In a particularly preferred embodiment said NK-differentiation medium comprises between 0,2 ngram/ml and 2 ngram/ml IL-12. Surprisingly it has been found that a lower concentration of IL-12 in a method of the invention results in a higher amount of CD56 positive cells. This increase in the number of cells can be significant as indicated in FIG. 2. A lower concentration also leads to a surprisingly higher purity of the collected CD56 positive cells. An NK-cell differentiation medium comprising a higher amount of IL-12 apparently results in a reduced number of replication cycles in a method of the invention. A NK-cell differentiation medium comprising a lower amount of IL-12 apparently results in an increase of the percentage of CD56 positive cells from the CD34 positive cells at the initiation of the culture step iii). The inventors have found that the percentage of CD56 positive cells that also express another marker of NK-cells such as preferably NKG2A, CD62L, CD16 and/or KIR is not significantly affected at the preferred concentrations of IL-12.

The cell density is preferably $0,1 \times 10^6 - 10 \times 10^6$ cells/ml, more preferably $0,5 \times 10^6 - 5 \times 10^6$ cells/ml. In a particularly preferred embodiment the cell density is $1 \times 10^6 - 3 \times 10^6$/ml. The indicated cell density is preferred for to start the culture step of step ii) and/or step iii) with. However, in a preferred embodiment the cell density is adjusted at least once during culture to the indicated densityIn a particularly preferred embodiment the cell density is maintained at the indicated density during culture. Considering the increase in cell numbers, adjustment or maintenance of the cell density is achieved by increasing the volume of the culture medium during culture. Maintenance in this context means keeping the cell density within the indicated range.

Culture step ii) and culture step iii) can be performed in a culture medium that comprises 0%-20% serum. The culture medium of step ii) preferably comprises from 0%-20% serum, more preferably 2%-10% serum. The NK-cell differentiation medium of step iii) preferably comprises between 0%-20% serum. In a preferred embodiment the NK-cell differentiation medium of step iii) comprises between 0%-10% serum. In a particularly preferred embodiment the NK-cell differentiation medium of step iii) comprises 0%-2% serum. In a preferred embodiment said serum is human serum.

The invention further comprises a collection of cultured NK-cells obtainable by a method for producing NK cells of the invention. The obtained and harvested cells can be used for transplantation purposes. Such transplantation is preferably performed for the treatment of any kind of human disease preferably all malignant diseases such as tumors, cancer, leukemia as well as all viral diseases, also in solid transplant rejection situations and autoimmune diseases and loss of pregnancy The invention further provides an in vitro collection of cells derived from a method for producing NK-cells of the invention. The collection of cells preferably consists of cells wherein at least 20% of the CD56 positive cells express CD62L; at least 10% of the CD56 positive cells express KIR; or at least 20% of the CD56 positive cells express CD16.

In a preferred embodiment the collection of cells derived from a method for producing NK-cells of the invention consists of cells wherein at least 50% of the CD56 positive, NKG2A positive and CD33 positive cells are positive for both KIR and CD62L.

The invention further provides a collection of storage containers for mammalian cells, wherein each of said storage containers contains cells derived from a culture of stem cells, progenitor cells or both, from human postembryonic tissue containing a plurality of NK cells or NK progenitor cells or both, obtainable by a method of the invention. In a preferred embodiment said collection of storage containers comprises at least 5 containers that each contains at least $4 \times 10E^8$ NK cells or NK progenitor cells or both. In a preferred embodiment said NK cells and/or NK progenitor cells comprise cell surface markers as indicated herein. In a preferred embodiment said containers comprise harvested cells from a culture that was initiated by cells from a single source, i.e. a single human individual. Typically such cells are genetically identical. This has the advantage that quality control can be performed on a separate sample. Furthermore, storage in separate containers allows for sequential administration of the graft to a human in need thereof. If the individual responds well the administration of a graft, a subsequent graft can be selected having the same properties as the graft that the individual had already been treated with. To this end the invention further provides a cell bank comprising a collection of cultured cells derived from a culture of stem cells, progenitor cells or both from human postembryonic tissue, containing a plurality of NK cells or NK progenitor cells or both, obtainable by a method of the invention or comprising a collection of storage containers according to the invention.

NK cells or progenitor cells thereof have different properties depending on the developmental stage or cell surface markers expressed by the NK-cells or progenitor thereof. The NK-cells that are produced with a method of the invention are particularly cytotoxic and exert higher antibody dependent cytotoxicity than NK cells produced in a different manner. The NK cells of the present invention have a higher expression of CD62L than freshly obtained NK-cells and are better suited for homing NK-cells to lymph nodes. The NK cells of the present invention also invade or enter the tissue better than freshly obtained NK cells. The NK-cells of the present invention also express more KIR and exhibit improved NK-cell function in a KIR ligand mismatched donor to patient setting. NK-cells obtained by a method of the invention are also particularly suited for migration to specific sites in the body. For instance, the NK-cells of the present invention home to the bone marrow, lymph nodes, liver, spleen and lungs.

The invention further provides a method for killing a cancer cell with NK-cells, said method characterized in that said NK-cells comprise NK cells obtainable or obtained with a method for producing NK cells of the invention, or comprise NK-cells of a collection according to the invention. The invention further provides a collection of NK-cells produced by a method for producing NK-cells of the invention, for use in the treatment of cancer, of a viral disease, of a solid transplant rejection, of an autoimmune disease and a loss of pregnancy. In a preferred embodiment said use in the treatment of cancer further comprises treatment with an antibody specific for an antigen present on cells of said cancer. In a preferred embodiment said antibody is a therapeutic monoclonal antibody such as Rituximab (anti-CD20), Trastuzumab (anti-Her2), Alemtuzumab (anti-CD52), Cetuximab (anti-EGFR), evacizumab (anti-VEGFA), Panitumumab (anti-EGFR), Ofatumumab (anti-CD20), Gemtuzumab (anti-CD33), Ibritumomab (anti-CD20), Dacetuzumab (anti-CD40), Tremelimumab (antiCTLA-4), Ipilimumab (anti-CTLA4), OX86 (anti-OX40), CT-011 (anti-PD1), BMS-663513 (anti CD137), Daclizumab (anti-CD25) or Tositumomab (anti-CD20), in a particularly preferred embodiment said antibody is an anti-CD20 antibody.

In a preferred embodiment said cancer is a skin cancer, breast cancer, lung cancer, ovarian cancer, fallopian tube cancer, colorectal cancer, head and neck cancer, prostate cancer, bladder cancer, liver cancer, pancreatic cancer, stomach cancer, esophagus cancer, brain cancer, In a preferred embodiment said skin cancer is a melanoma.

In a preferred embodiment said cancer is a cancer of hematopoietic origin like leukemia such as acute myelogenous leukemia (AML), acute lymphoblastic leukemia (ALL), chronic myelogenous leukemia (CML), chronic lymphocytic leukemia (CLL), acute monocytic leukemia (AMOL) and lymphomas such as Hodgkin's and Non-Hodgkin's Lymphomas and their subtypes or multiple myeloma.

The previously established as well as the IL-12 modulated ex vivo hematopoietic stem cell (HSC) expansion and NK cell differentiation method is shown. In the basic protocol CD34+ UCB cells were expanded by SCF, IL-7, TPO, Flt3L, G-CSF, GM-CSF, IL-6 and low molecular weight heparin for 10 days, followed by the differentiation of CD56+ NK cells by replacement of TPO with IL-15 at day 10 and Flt3L and the low molecular weight heparin by IL-2 at day 14. For the modulation of the culture system with IL-12, at day 10 of culture NK cell differentiation was induced by IL-15 alone (a) or by IL-15 and IL-12 (b). Cells were grown up to a total of at least 28 days.

Figure 2:
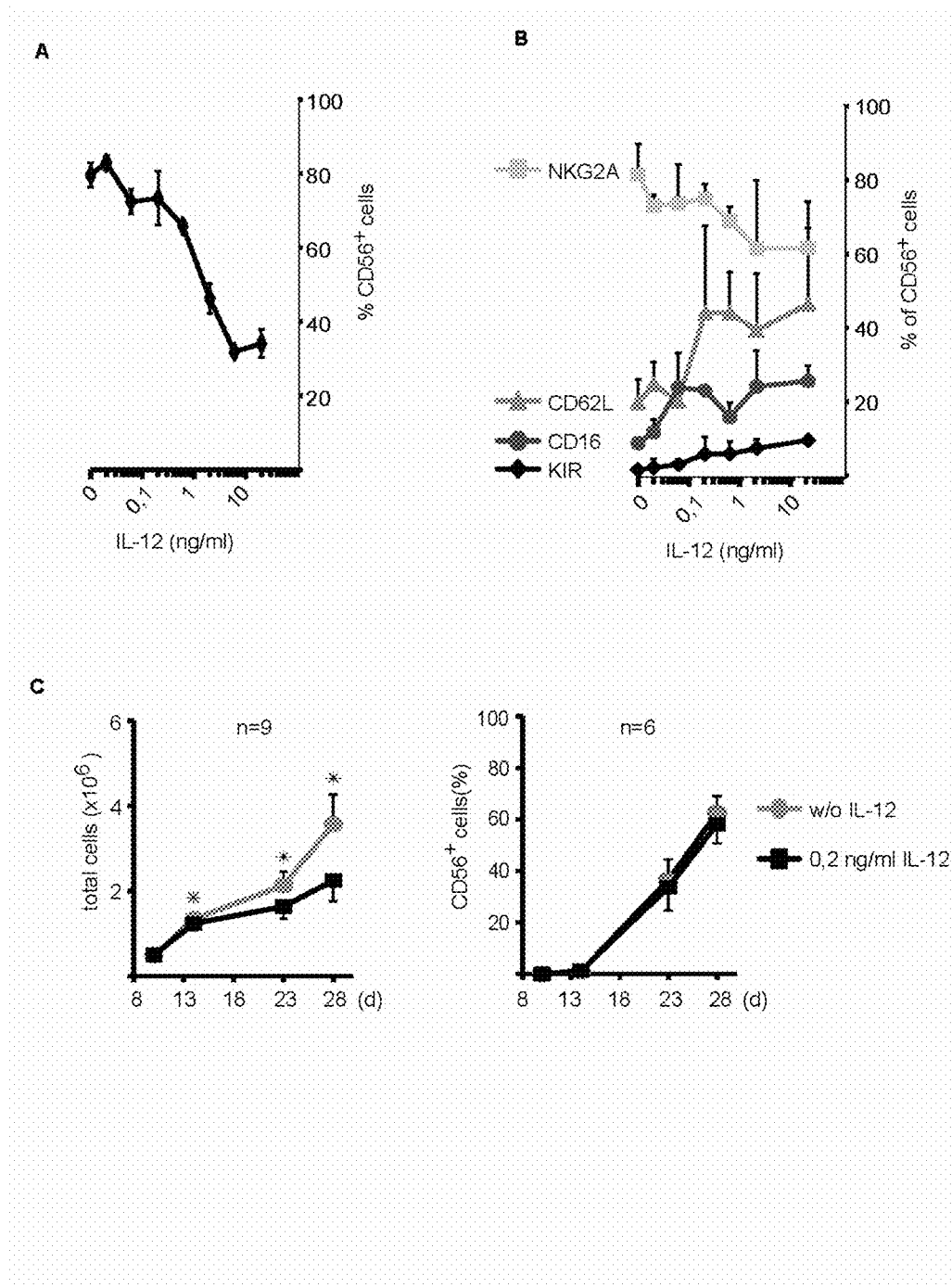

FIG. 2. Effects of IL-12 on the phenotype and the purity of ex vivo generated NK cells.

Effects of high and low dose IL-12 on the ex vivo NK cell generation culture and the NK cell phenotype were analyzed by flow cytometry and cell counting. In a titration analysis the effect of low (10 pg/ml) to high (20 ng/ml) concentrations of IL-12 on NK cell purity (A) and NK cell receptor expression (B) were determined by cell counting and flow cytometry analysis for CD56 expression and NKG2A CD62L, CD16 and KIR expression on CD56+ cells. Values are shown as mean±SD calculated from triplicate wells for one representative experiment at day 22 of culture.

(C) A concentration of 0,2 ng/ml IL-12 was chosen for further experiments and analyzed at day 29 of culture for reduction in total cultured cells and CD56+ NK cell purity by cell counting and flow cytometry for CD56+ cells. Mean percentage±SEM for several independent cultures (n) are shown as indicated.

Figure 3:
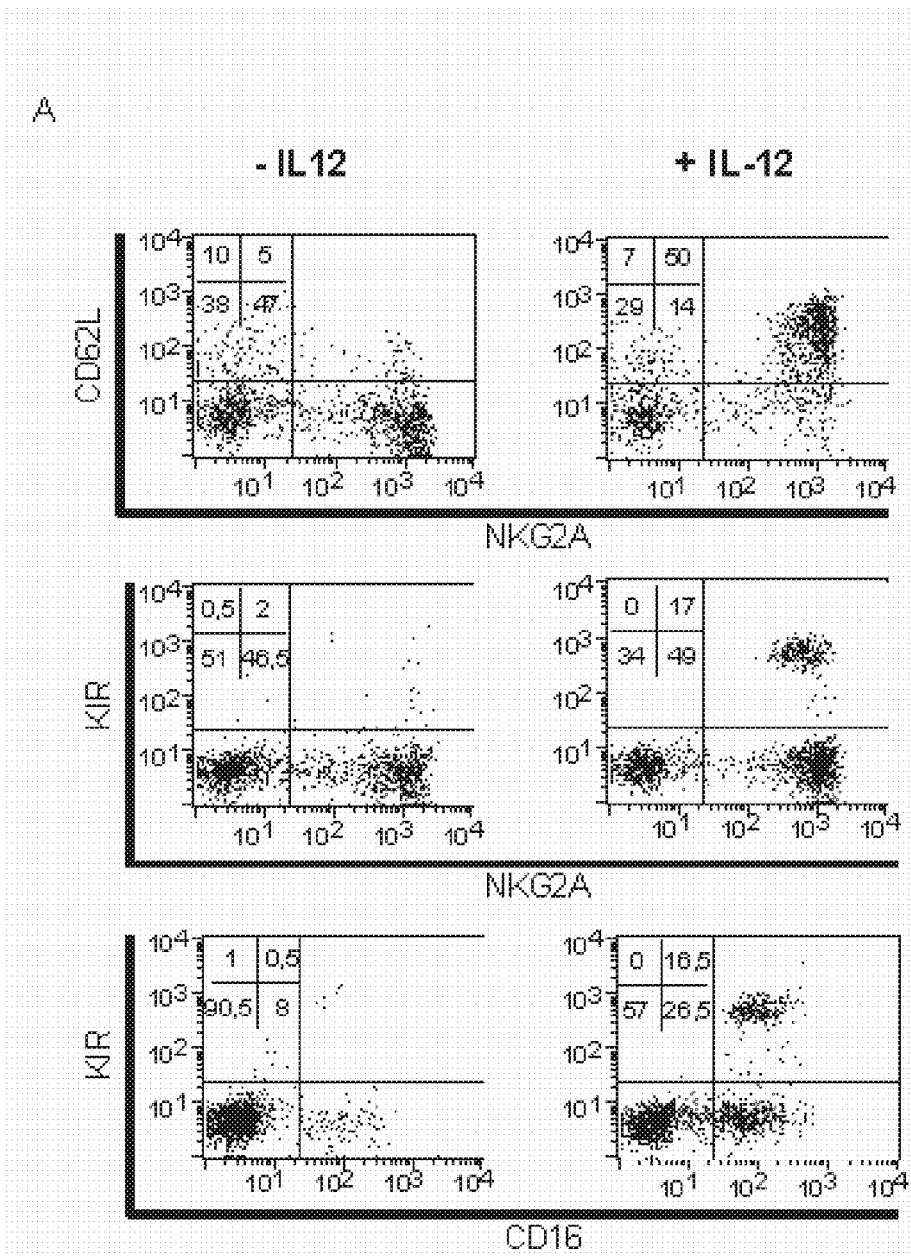
Figure 3:
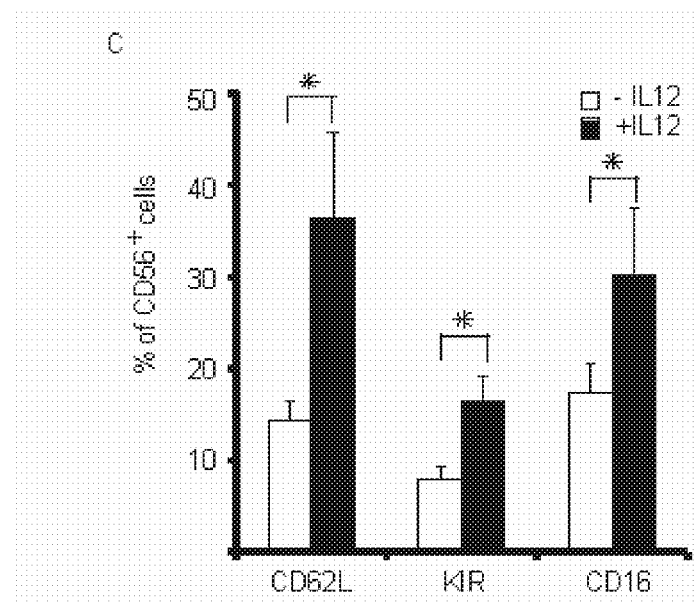

FIG. 3. Comparison of receptor expression correlated with cytotoxicity and homing on ex vivo with and without IL-12 differentiated NK cells.

The effect of 0,2 ng/ml IL-12 on the expression of several NK cell antigens was determined by flow cytometry analysis at day 29 of ex vivo differentiation. Flow cytometry dot plots depicting the expression of CD62L, KIR, CD16 and NKG2A on gated CD56+ cells (A) as well as for CCR1, CCR6-8 and CD56 (B) are shown for one representative ex vivo NK cell differentiation culture induced with and without IL-12. The statistical comparison, determined by flow cytometry analysis for 5 independently performed experiments of ex vivo NK cell differentiation generated with or without 0,2 ng/ml IL-12, is displayed for CD62L, KIR and CD16 as mean percentage ±SEM (C).

Figure 4:
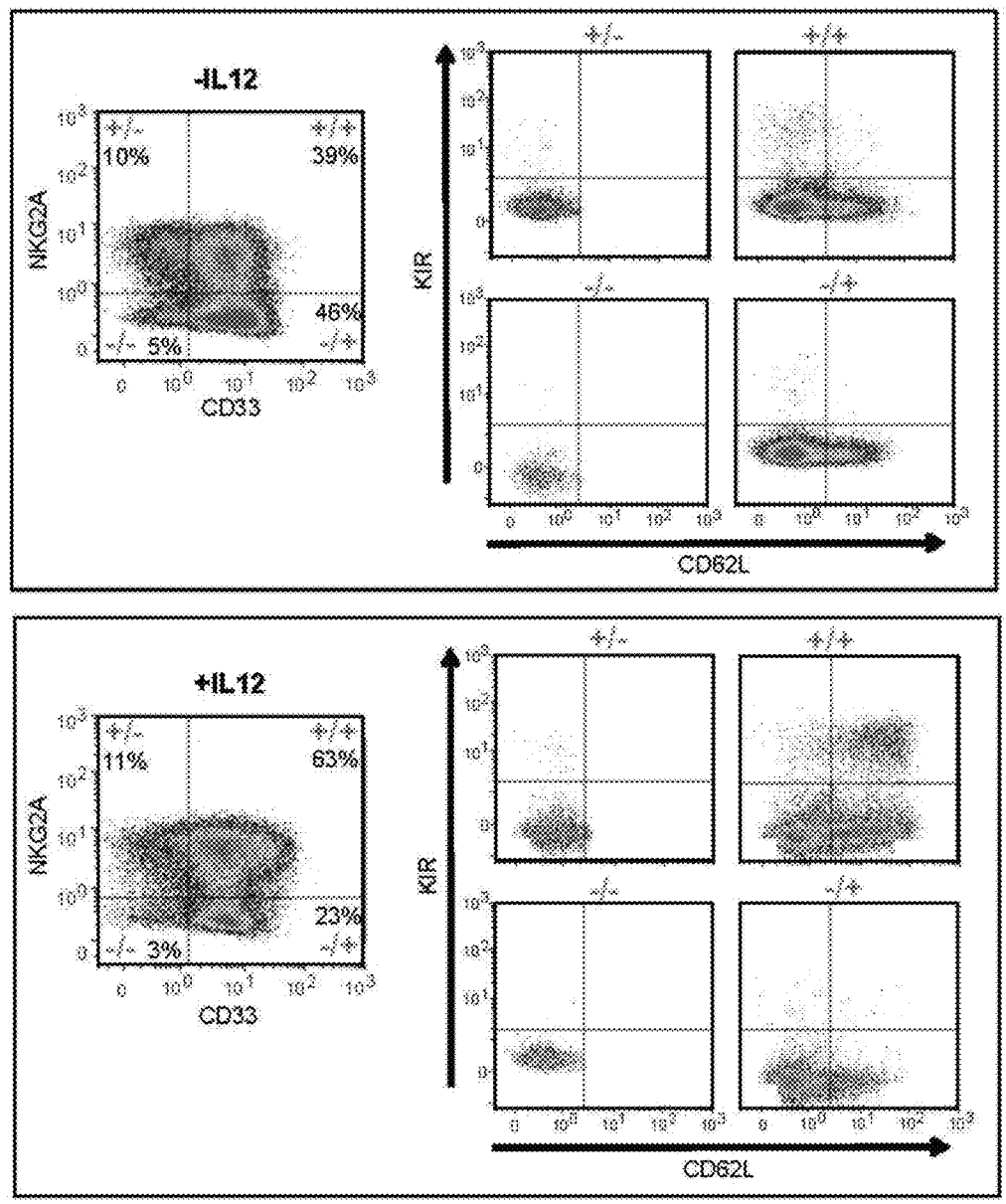

FIG. 4. Effect of IL-12 on distinct CD33 and NKG2A determined stages of NK cell differentiation.

Ex vivo with or without 0,2 ng/ml IL-12 differentiated NK cells were analyzed for their CD33 and NKG2A maturation profile at day 28 of culture. Comparative flow cytometry dot plots revealing the expression of CD33 and NKG2A are shown on the left upper panels indicating the gates for CD33+/NKG2A−, CD33+/NKG2A+, CD33−/NKG2A+ and CD33−/NKG2A− cells that were further analyzed for KIR and CD62L expression in the consecutive boxed panels. A representative example of 3 cultures analyzed is shown.

Figure 5:
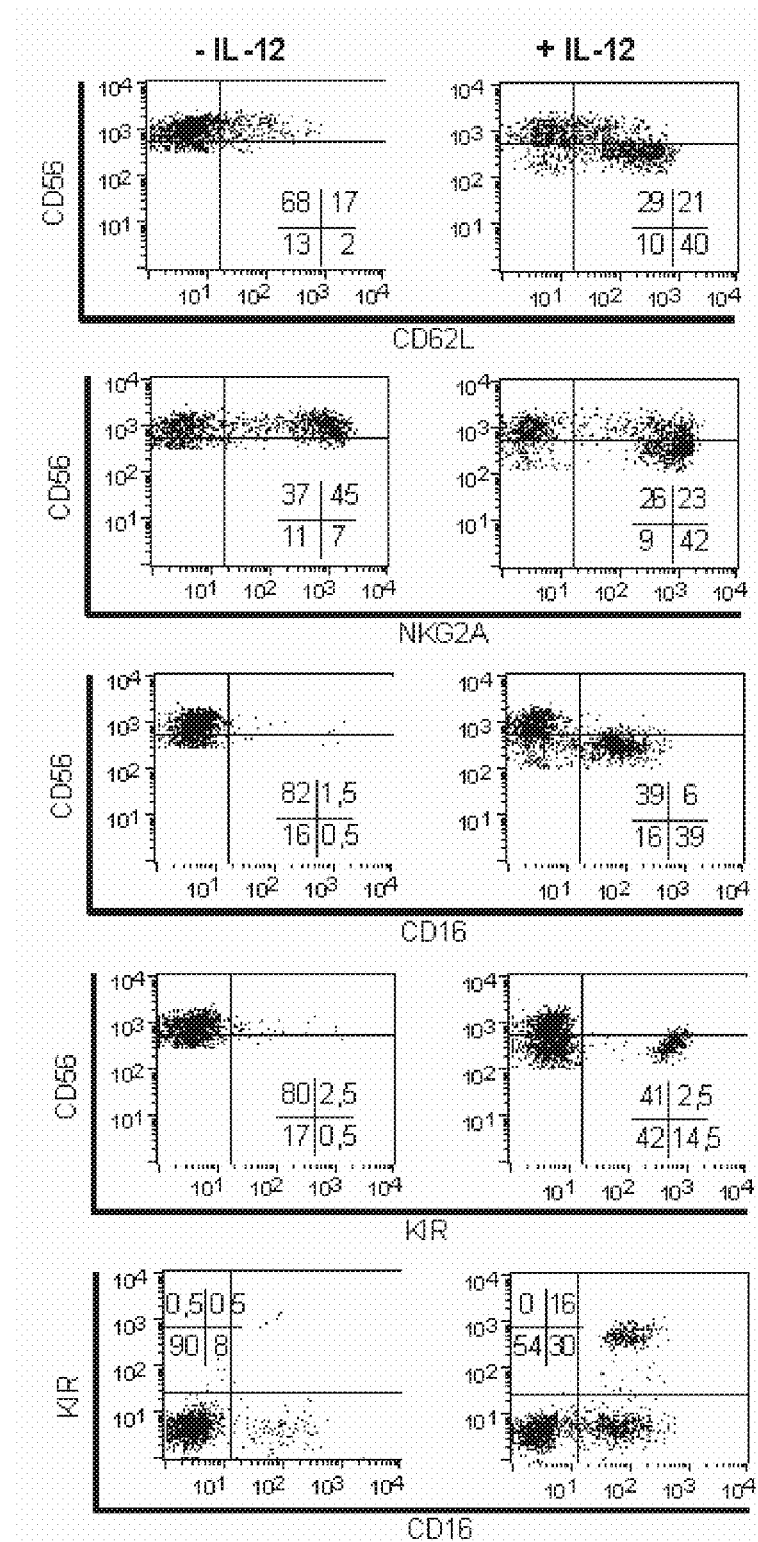

FIG. 5. CD56 expression profile of ex vivo differentiated IL-12 modulated NK cells.

The expression level of CD56 in correlation with CD62L, NKG2A, KIR and CD16 was compared in flow cytometry analysis for gated CD56+ ex vivo differentiated NK cells with or without IL-12 modulation during culture. One representative experiment is shown that revealed particular strong induction levels for CD62L, KIR and CD16.

Figure 6:
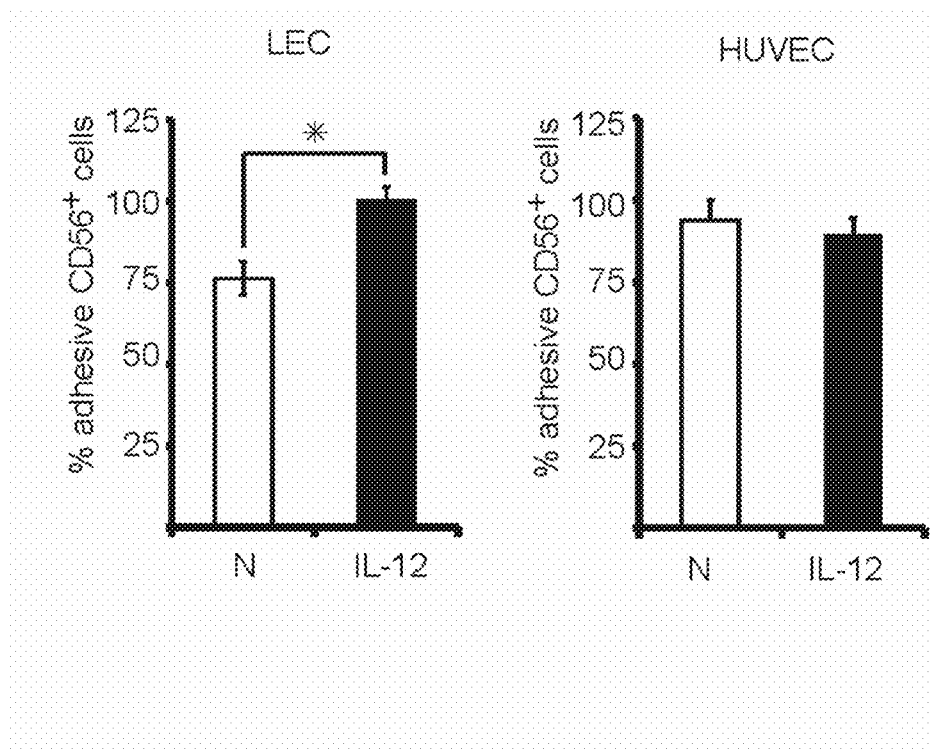

FIG. 6. Analysis of adhesive and migratory capacities of ex vivo differentiated and IL-12 induced NK cells.

(A) Comparison of ex vivo generated NK cells, that were generated with or without 0,2 ng/ml IL-12, for adhesion to lymphatic endothelial cells. Ex vivo generated NK cells from day 28 of culture were purified and subsequently used in adhesion assays on lymphatic endothelial cells (LecT-ERT) or human umbilical vein endothelial cells (HUVEC). Mean percentage values±SEM calculated from 3 independent experiments each performed in duplicate are shown.

Figure 7:
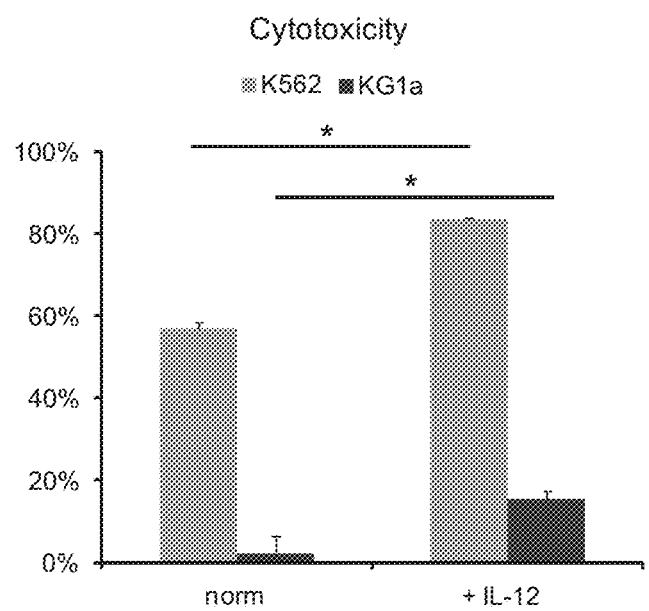
Figure 7:
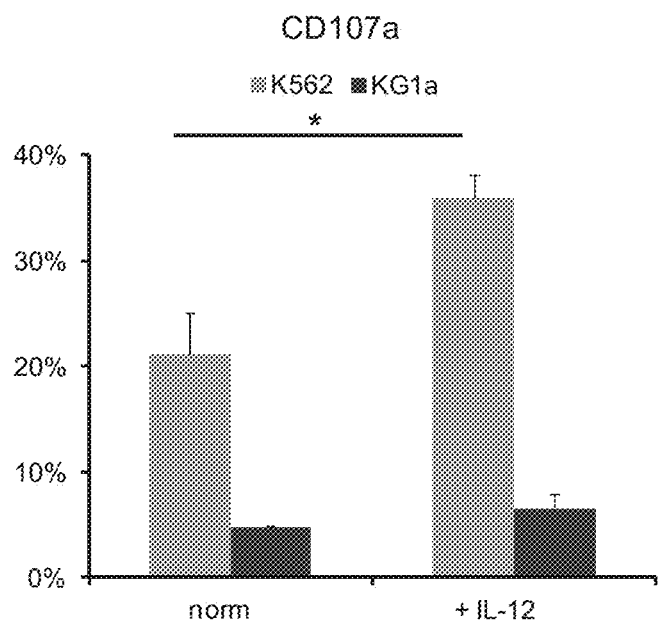

FIG. 7. Cytotoxic capacities of ex vivo differentiated NK cells in correlation with IL-12 modulation during culture.

NK cells stimulated with or without IL-12 were cultured with K562 (light grey bars) or KGla (dark grey bars) at an effector: target ratio (E:T ratio) from 1:1 overnight for 18 h. Co-cultures were analyzed for cytotoxicity (A) or CD107a degranulation (B).

Figure 8:
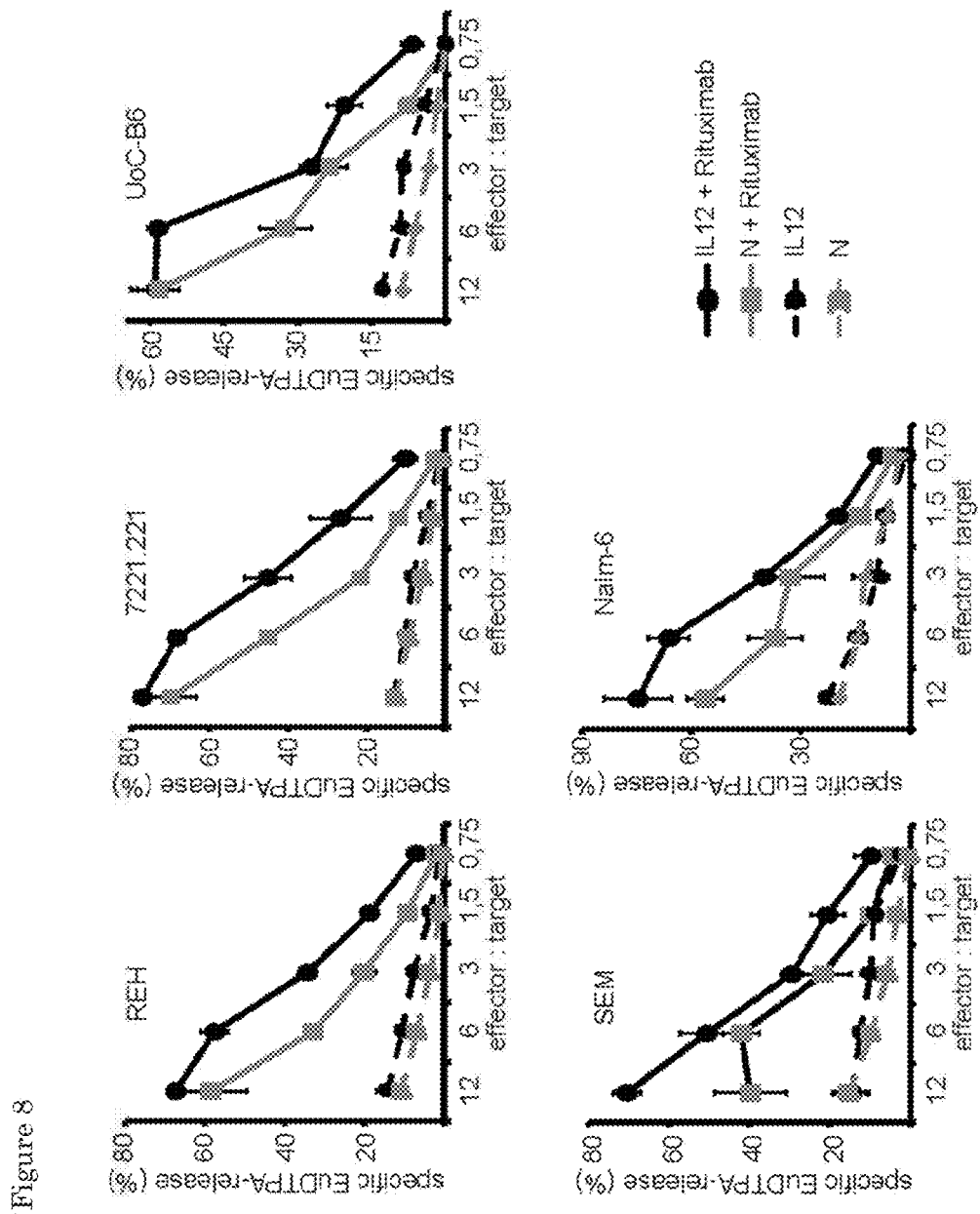

FIG. 8. Relation of enhanced antibody-dependent-cytotoxicity and IL-12 modulation during ex vivo NK cell generation.

Ex-vivo generated NK cells from day 28 of culture with and without induction of 0.2 ng/ml IL-12 were purified and subsequently used in Europium-release killing assays. B-cell target cell lines 7221.221, REH, UoCB6, Nalm-6 and SEM were used at several effector to target ratios and previously labeled with the therapeutically used antibody Rituximab if indicated. Mean values±SD calculated from triplicate wells are shown for a representative experiment performed.

Figure 9:
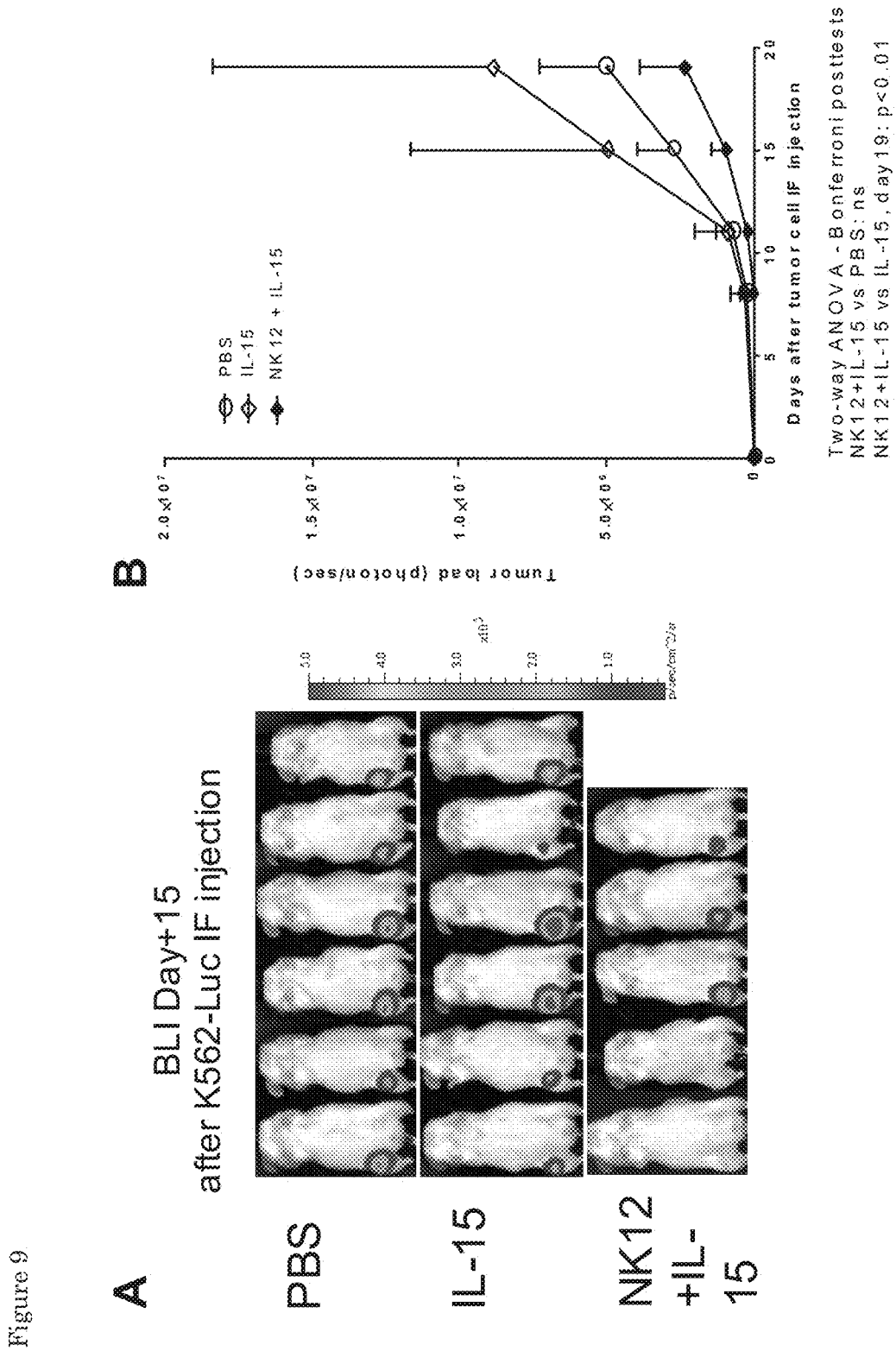
Figure 9:
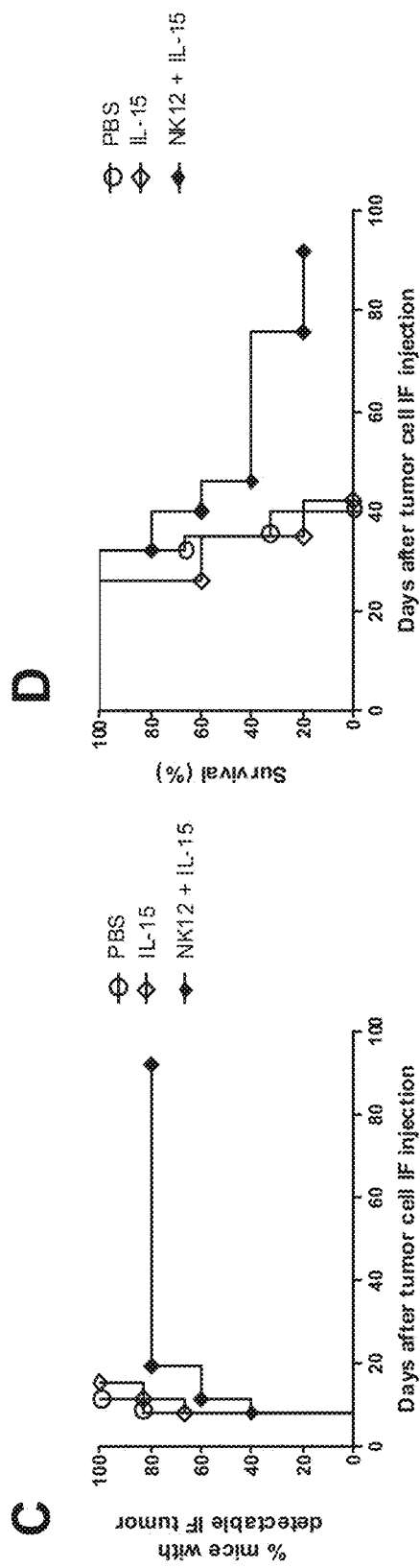

FIG. 9: UCB-NK cells in combination with rhIL-15 mediate anti-leukemic response in vivo.

Adult NSG mice were injected in their right femur with $10^5$ Luciferase-expressing K562 AML cells. The day after, mice were treated with $20\times10^6$ UCB IL-12-NK cells i.v. combined with IL-15 i.p. administration (0.5 microgram/mouse i.p. every 2-3 days for 14 days), or received PBS or IL-15 alone as control (n=6 per group). Tumor load was monitored by bioluminescence imaging from day 8 after AML cell inoculation and next every 3-4 days. (A) BLI at day 15 after tumor cell injection. (B) In vivo tumor load follow-up by BLI, mean±SD (C) Time to first tumor detection (D) Survival curve

EXAMPLES

Materials and Methods
CBMC Isolation and Enrichment of CD34+ Stem and Progenitor Cells Human umbilical cord blood (UCB) samples have been obtained at birth after normal full-term delivery and written informed consent with regard of scientific use and were supplied by VivoCell Biosolutions AG (Graz, Austria) within AKH Wien, Austria or from the cord blood bank of the Radboud University Nijmegen Medical Center (RUNMC, Nijmegen, The Netherlands). Mononuclear cells were isolated by density gradient centrifugation (LSM 1077 Lymphocyte Separation Medium, PAA Laboratories GmbH, Graz, Austria) and labeled with CliniMACS CD34 reagent (Miltenyi Biotech, Bergisch-Gladbach, Germany). The CD34+ cell selection was performed according the manufactures instructions and after the enrichment procedure, the CD34+ cell fraction was collected, and the cell number and purity were analyzed by flow cytometry. Finally, the obtained CD34+ UCB cells were used directly for the NK cell generation bioprocess.

Ex vivo Expansion and Differentiation of CD34+ Progenitor Cells

CD34+ UCB cells were transferred into culture plates and expanded and differentiated according to culture method III as described previously[15]. In short, UCB cells were labeled with CliniMACS CD34 reagent (Miltenyi Biotech, Bergisch-Gladbach, Germany) and CD34+ cells were selected by magnetic isolation (Miltenyi MACS Separator) according instructions of the manufacturer. CD34+ cells were collected, cell number and purity established by flow cytometry and the cells used for NK cell generation. CD34+ UCB cells were transferred into culture plates and expanded and differentiated according to culture method III as described previously[15]. In short, CD34+ cells were expanded for 10 days in GBGM® supplemented with a high dose of the factors SCF (27 ng/ml, CellGenix, Freiburg, Germany), IL-7 (25 ng/ml, Stemcell Technologies, Grenoble, France), TPO (25 ng/ml, Stemcell Technologies), Flt3L (25 ng/ml, CellGenix) and a low dose of the factors G-CSF (250 pg/ml, Stemcell Technologies), GM-CSF (10 pg/ml, Stemcell Technologies) and IL-6 (50 pg/ml, CellGenix) as displayed in FIG. 1A. Differentiation was induced by replacing TPO by IL-15 (20 ng/ml, CellGenix) at day 10 and Flt3L by IL-2 (1000 U/ml, Chiron, Munchen, Germany). During the first 14 days of culture low molecular weight heparin (25 mg/ml, Abbott, Wiesbaden, Germany) was included in the growth medium. Cells were grown up to a total of at least 28 days.

For induction, rh-IL12 (Immunotools, Friesoythe, Germany) was added from day 10 on at a concentration of 0.2 ng/ml (if not indicated differently). For functional studies the ex vivo generated NK cells were purified with CD56 microbeads (Miltenyi Biotec) according the manufactures instructions and directly used in functional assays.

Cell Lines

Cell line K562 (LGC Standards, Wesel, Germany) was cultured in Iscove's modified Dulbecco's medium (IMDM; Invitrogen, Carlsbad Calif., USA) containing 50 U/ml penicillin, 50 µg/ml streptomycin and 10% fetal calf serum (FCS; Integro, Zaandam, the Netherlands). Human B cell precursor leukemia cell lines 721.221, SEM, REH, Nalm-6 and UoC-B6 were cultured in RPMI-1640 (Sigma-Aldrich, Vienna, Austria) containing 50 U/ml penicillin, 50 µg/ml streptomycin (PAA Laboratories GmbH, Graz, Austria) and 10% fetal calf serum.

Lymphatic endothelial cells stably transfected with hTERT (LecTERT) were kindly provided by Prof. Dr. Dontscho Kerjaschki AKH Vienna, Austria, cultured in DMEM medium (Invitrogen, Fisher Scientific GmbH, Vienna, Austria) containing 50 U/ml penicillin, 50 µg/ml streptomycin (PAA Laboratories GmbH, Graz, Austria) and 20% fetal calf serum and were selected with 100 µg/ml Hygromycin (Invitrogen, Fisher Scientific GmbH, Vienna, Austria).

Human umbilical vein endothelial cells (HUVECs) were isolated as described previously[28] and cultured in EGM-2 medium (Bio Whittacker, Lonza, Verviers, Belgium).

Flow Cytometry

Cell numbers and expression of cell-surface markers were determined by flow cytometry. For immunophenotypical staining, cells were after incubation with FcR-blocking reagent (Miltenyi Biotec), incubated with the appropriate concentration of antibodies for 30 min at 4° C. After washing, expression was measured using a FACSCalibur and analyzed with CellQuestPro software (both from BD Biosciences). To determine purity and phenotype of the cultured cells following antibodies were used: CD3-FITC clone UCHT1 (Immunotools), CD56-APC clone NCAM16.2 (BD Biosciences), NKG2A-PE clone Z199.1.10 (Beckman Coulter), CD16-PE clone 3G8 (BD Biosciences), CD62L-FITC clone LT-TD180 (Immunotools), KIR-FITC clone 180704 (R&D Systems), CXCR3 (R&D Systems), CXCR4 (Biolegend), CXCR5 (R&D Systems), CCR1 (R&D Systems), CCR7 (R&D Systems), CCR6 (Biolegend).

Adhesion Assay

Ex vivo generated and purified NK cells were transferred onto confluent LecTERT cells and incubated in RPMI-1640 for 30 min at RT on a belly dancer. After extensive washing, cells were trypsinized, stained with CD56-APC and analyzed as described under Flow Cytometry.

Cytotoxicity Assay

Flow cytometry-based cytotoxicity assays were performed as described previously[14, 15]. Briefly, after incubation for 4 h or overnight at 37° C., 50 µl supernatant was collected and stored at −20° C. for later use to measure cytokine production. Cells in the remaining volume were harvested and the number of viable target cells was quantified by flow cytometry. Target cell survival was calculated as follows: % survival={[absolute no. viable CFSE+ target cells co-cultured with NK cells]/[absolute no. viable CFSE+ target cells cultured in medium]}*100%. The percentage specific lysis was calculated as follows: % lysis={100−[% survival]}. Degranulation of NK cells during co-culture was measured by cell surface expression of CD107a[29]. After 18 hrs of incubation at 37° C., the percentage of CD107a+ cells was determined by flow cytometry.

Antibody-Dependent-Cytotoxicity Assay Using Rituximab

The antibody-dependent cytotoxic activity against several human B cell precursor leukemia cell lines 721.221, SEM, REH, Nalm-6 and UoC-B6 was measured in triplicates within a Europium-release killing-assay as described previously[30]. Target cells were labelled with EuDTPA (europium diethylenetriaminepentaacetate), subsequently washed and incubated with 10 µg/ml Rituximab (kindly provided by AKH Vienna, Austria) for 1 h at RT. After extensive washing 2×10³ target cells were incubated for 4 h with purified NK effector cells at various E:T ratios in RPMI-1640 without phenolred (PAA Laboratories, Pasching, Austria) supplemented with 10% FCS. Maximal EuDTPA release was determined by incubation with 1% Triton X-100. Values for specific release of EuDTPA were determined with Delfia Enhancement Solution (Perkin Elmer, Brunn am Gebirge, Austria) via time-resolved fluorescence. The specific cytotoxicity was calculated as percent specific EuDTPA release= (Mean sample−Mean spontaneous release)/(Mean maximal release−Mean spontaneous release)×100.

Statistics

Results from experiments performed in triplicates are described as mean±standard deviation of the mean (SD). Results from individual experiments are shown as mean±standard error of the mean (SEM). Statistical analysis was performed using Student's t-test. A p-value of <0.05 was considered as statistically significant.

Results

Figure 1:
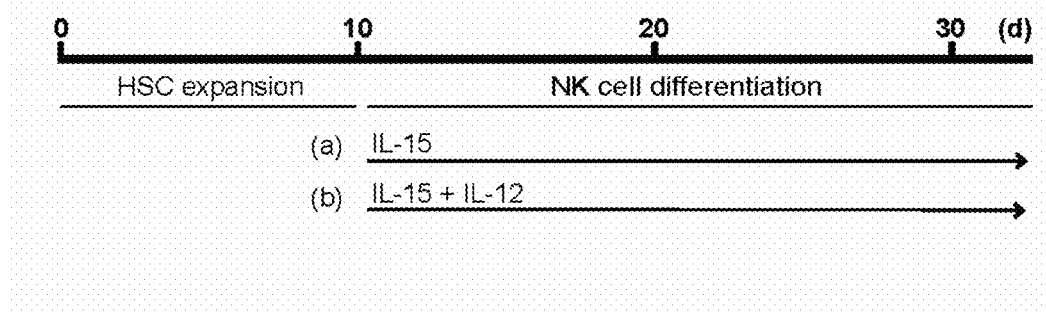
FIG. 1. Scheme of established and modulated ex vivo NK cell differentiation protocol.

Low Dose IL-12 Enhance Expression of CD16, KIR and CD62L NK Cell Antigens During Ex Vivo NK Cell Differentiation Initially, we aimed to analyze the impact of a various of cytokines like IL-12, IL-18 or IL-21 on our recently established and characterized ex vivo human NK cell differentiation method in addition to the use of IL-15 and IL-214, 15, to lead to a tailored NK cell phenotype. For the cytokines IL18 and IL-21 we have not found a significant improvement regarding expansion or activation of the ex vivo generated NK cell product (data not shown). However, we found that low doses of IL-12 could significantly modify the NK cell generation procedure. During culture, at day 10 after expansion of hematopoietic stem cells IL-15 and IL-12 were simultaneously added to induce NK cell differentiation (FIG. 1). We analyzed in detail the effect on NK cell differentiation of different IL-12 concentrations ranging from 10 pg/ml to 20 ng/ml. The percentage of NK cells within the culture system decreased with increasing concentrations of IL-12 (FIG. 2A), whereas the expression of CD62L, CD16 and KIR on CD56+ NK cells was elevated with higher doses of IL-12 (FIG. 2B). This dose-response analysis revealed that a concentration of 0.2 ng/ml IL-12 was enough to significantly enhance surface receptor expression on the ex vivo generated NK cells, but does not result in a significant lower purity of the final NK cell product (FIG. 2A). Having selected the most optimal IL-12 concentration purity and further experiments revealed, that the overall impact of 0.2 ng/ml IL-12 on the culture system reveals a tolerable reduction in total cell counts rather than an impact on the NK cell purity itself (FIG. 2C).

After we determined the optimal concentration of IL-12 we analyzed in more detail the impact of this cytokine on the phenotype of the ex vivo differentiated NK cells. On account of the potential therapeutical use of the ex vivo generated NK cells we focused our observations on receptors that are related to the cytotoxic activity of NK cells and receptors that are relevant for migration abilities of NK cells. Firstly, IL-12 enhanced the expression of the activating antibody-dependent-cytotoxicity receptor FcRγIII/CD16 and the expression levels of KIRs compared to NK cells generated with the basal culture system (FIG. 3A). Secondly, L-Selectin and a specific chemokine receptor repertoire of CCR6, CCR7, CXCR3, CXCR4 and CXCR5 exhibited high expression on IL-12 modulated ex vivo differentiated NK cells (FIG. 3B). In summary, the overall phenotype of NK cell modulated with IL-12 during ex vivo differentiation reveals a tailored generation of NK cells expressing CD62L, CD16, KIR, CCR1, CCR6, CCR7, CXCR3, CXCR4 and CXCR5.

IL-12 Forces a Faster Transition of CD33+NKG2A− Towards CD33+NKG2A+CD56+ NK Cells of Development Stages Within the Ex Vivo NK Cell Differentiation Culture NK cell are classically divided into CD56$^{bright}$ and CD56$^{dim}$ NK cells, which both exhibit specialized receptor expression and correlated functions. The influence of IL-12 on the expression of CD62L and particularly KIR and CD16 posed the question if this phenotype is correlated with a more mature stage of NK cell differentiation, since these NK cell antigens are most prominently expressed on the mature CD56$^{dim}$ peripheral blood NK cells. Recently, we described NK cell developmental subsets described by the expression of CD33 and NKG2A[31]. When we compared the composition of development stages determined by the expression of CD33 and NKG2A we observed a higher proportion of the more mature CD33+NKG2A+ NK cells in IL-12 modulated (63%) than normal cultures (39%) but a lower percentage of CD33+NKG2A− (23% vs. 46%) CD56+ NK cells (FIG. 4). Furthermore, the enhanced expression of CD62L and KIR observed within this enlarged proportion of CD33+ NKG2A+ NK cells emphasizes that a higher proportion of the IL-12 induced ex vivo generated NK cells reside in an advanced developmental stage (FIG. 4, boxed panels).

In IL-12 modulated NK cell differentiation cultures exhibiting particular high induction levels of CD62L, CD16 and KIR we could also identify a correlation with the appearance of a CD56$^{dim}$ phenotype. Flow cytometry analysis revealed, that some cultures exhibited CD56$^{dim}$ NK cells accountable for the enhanced CD62L, CD16 and KIR expression by the ex vivo generated CD56+ NK cells (FIG. 5). All together these data indicate an advanced NK cell differentiation inducible by IL-12.

Ex vivo with IL-12 Generated NK Cells Show Improved Adhesive Function on Lymphatic Endothelial Cells The molecules involved in adhesion to lymphatic tissues, namely CD62L, and the chemokine receptors CCR1 and CCR6-8 allowing migration towards chemokine gradients thereby guiding migration into tissues, showed elevated expression on IL-12 modulated NK cells. Therefore, we performed in vitro assays to examine whether the IL-12 induced NK cell phenotype correlates with better adhesion in response to lymphoid tissues (FIG. 6). Assays comparing the adhesion to human umbilical vein endothelial cells (HUVEC) or lymphatic endothelial cells (LEC) showed that IL-12 induced ex vivo differentiated NK cells significantly better adhered to LEC than HUVEC cells, whereas not IL-12 modulated NK cells exhibited no enhanced adhesion to LEC compared to HUVEC cells (FIG. 6).

In summary these data reveal, that the modulation of NK cell differentiation by IL-12 leads to NK cells with improved adhesive that could exert certain migratory abilities potentially allowing increased homing to various tissues.

IL-12 Modified Ex Vivo Generated NK Cells Exert a Stronger Killing Capacity Towards AML Targets And Revealed Enhanced Antibody-Dependent-Cytotoxicity Reactions Owing to the enhanced KIR expression and advanced differentiation stage of the IL-12 induced ex vivo generated NK cells we aimed to analyze if this might correlate with enhanced cytotoxicity in in vitro killing assays (FIG. 7). Assays combining an analysis of killing efficiency and CD107a-activity against the MHC class I-negative, classical target cell line K562 and the MHC class I-positive cell line KGla revealed better recognition and activity of the IL-12 modulated compared to not IL-12 induced ex vivo generated NK cells (FIG. 7 A and B).

The enhanced CD16 expression of the NK cells differentiated under IL-12 modulation supposes an influence on their antibody-dependent-cytotoxicity (ADCC). The availability of therapeutical antibodies against many different human malignancies raised the question if the effect of these antibodies can be combined and enhanced with the cytotoxicity of the IL-12 modulated ex vivo generated NK cells. Hence, we compared the killing efficiency of ex vivo with or without IL-12 induction generated NK cells for their killing efficiency against several B-cell-lines pre-treated with the therapeutic B-cell-specific antibody Rituximab (FIG. 8). All B-cell lines tested, namely 721.221, REH, SEM, Nalm-6 and UoC-B6, were significantly better lysed by NK cells when they were pre-treated with Rituximab. Moreover, IL-12 modulated NK cells exhibited better killing capacities against all Rituximab coated B-cell lines than ex vivo generated NK cells not induced with IL-12. These data on the enhanced cytolysis of malignant target cells treated with therapeutic antibodies and ex vivo with IL-12 differentiated NK cells reveal a new aspect and functionality of this combination of therapeutic agents. Therefore, ex vivo differentiated IL-12 induced NK cells reveal a presumable therapeutic impact of these cells in combination with the various available therapeutical antibodies.

Discussion

The recently established ex vivo differentiation system for large scale generation of human NK cells holds great potential for adoptive immunotherapies of cancer[14,15]. Nevertheless, a tailored and modulated NK cell generation towards specified phenotypes and functions would facilitate the therapeutical use of these cells in an even broader range of malignancies. We have therefore analyzed several cytokines for their impact on the ex vivo NK cell differentiation and found IL-12 to be an especially strong modulator within this process. Under the influence of IL-12 during ex vivo NK cell differentiation the generated NK cells acquired higher expression of the cytotoxicity related KIR and CD16 receptors as well as CD62L and a specific chemokine receptor repertoire of CCR6, 7 and CXCR3-5 receptors related to homing and migration capacities of NK cells. Importantly, the optimized IL-12 concentration ensured the purity of the NK cell product whilst allowing an enhanced NK cell phenotype correlated with improved corresponding functions.

Previous studies revealed the picture that IL-12 induced peripheral blood NK cells (PBNK) acquire CD56$^{bright}$ expression and exhibit mature and terminally differentiated NK cells, although discordant experimental findings led to this idea. On the one hand, IL-12 induced a CD56$^{bright}$ NK cell phenotype by up regulation of CD94 and CD62L and a down modulation of CD16[10]. On the other hand, it was shown that CD16·CD56+ PBNK cells treated with IL-12 in combination with IL-2 and IL-15 developed CD16 expression alongside with a CD56$^{bright}$ expression[32]. Nevertheless, these studies highlighted the impact of IL-12 on NK cell receptor expression and function. In contrast, others have dissected human NK cell subsets on the basis of CD56 and CD16 expression and suggested that CD56$^{bright}$ CD16+ NK cells represent an intermediate stage of NK cell maturation between CD56$^{bright}$ CD16− and CD56$^{dim}$ CD16+ NK cells already exhibiting full functional capacity[33]. Recently, we identified distinct stages of human NK cell development on the basis of CD33 and NKG2A expression[31]. Therefore, we can further strengthen the idea that IL-12 modulated ex vivo generated NK cells exhibit a more mature NK cell phenotype because of the increased proportion of CD33+ NKG2A+ NK cells and, at least in cultures with especially high receptor induction, arising CD56$^{dim}$ NK cell subpopulation. Furthermore, whereas CD16 and KIR expression and the increased proportion of CD33+NKG2A+ and CD56$^{dim}$ NK cells favour the idea of more mature NK cells, the induction of CD62L by IL12 during ex vivo NK cell differentiation is not contradictory. A recent study revealed that CD62L+ CD56$^{dim}$ PBNK cells exhibit the full functional repertoire of NK cell cytokine production and cytotoxicity and are likely also representing an intermediate stage of NK cell differentiation towards cytotoxic CD56$^{dim}$ (CD16+ KIR+) CD62L−NK cells[34].

CD62L is an important receptor guiding NK cells into and out of lymph nodes through interactions with ligands on high endothelial venules and e.g. the ligand Mannose Receptor (MMR) along afferent and efferent lymphatic endothelium[35, 36]. Moreover to adhesion molecules such as CD62L, specific chemokine receptors guide NK cells into lymphoid tissues and sites of tissue inflammation along chemotactic gradients. Therefore, also the induction of the CCR1, 6-7 and CXCR3-5 chemokine receptor repertoire on IL-12 induced ex vivo generated NK cells renders these cells with a potential of improved migratory functions, as we could already evidence in in vitro assays for the adhesion to lymphatic endothelial cells, which could be likely exploitable for therapies of lymphoid leukemia, lymphomas or solid tumors.

Early studies already indicated the potency of IL-12 to modulate the differentiation towards a cytotoxic and IFN-γ producing NK cell[16]. In recent years, studies evidenced these findings in patients with dysfunctions in IL-12-signaling pathways revealing the necessity of NK cell priming through IL-12 for the acquisition of functional activity[17]. The acquisition of cytotoxic and IFN-γ producing NK cell functions by IL-12 was already correlated with induced expression of the IFN regulating factor-1 (IRF-1) and perforin genes[18,19]. In line with this, our in vitro killing assays against the MHC class I-positive KG1a and the MHC class I-negative K562 cell line confirmed an enhanced cytotoxic activity of the IL-12 induced ex vivo differentiated NK cells and support their possibly enhanced impact in antitumor therapies. A characteristic of CD56$^{dim}$ NK cells is the ability to lyse antibody-coated target cells, a phenomenon named antibody-dependent-cytotoxicity (ADCC) which is mediated through the receptor CD16/FcRγIII. The enhanced expression of CD16 of ex vivo, under the influence of IL-12, differentiated NK cells might be utilized in therapeutic settings combining the cytotoxic activity of NK cells with therapeutic antibodies against malignant cells. Studies already revealed the potential and importance of e.g. the therapeutical antibody Rituximab recognizing CD20 on B-cell leukemias in combination with human PBNK cells[37, 38]. This substantiates the improved functional capacity and potential therapeutic utilization of the IL-12 modulated ex vivo differentiated NK cells in combination with therapeutic antibodies, which we could already confirm in in vitro ADCC-assays against several B-cell lines coated with Rituximab antibodies.

Altogether, our findings indicate that IL-12 is an auspicious modulator of NK cell differentiation that can be exploited to generate NK cells with specified phenotypes and functions. This furthermore holds great potential and promise for the additional use of these cells in therapies of solid, especially lymphoid tumors and in combinational clinical settings accompanying therapeutic antibodies.

REFERENCES

1. Cooper, M. A. et al. Human natural killer cells: a unique innate immunoregulatory role for the CD56(bright) subset. *Blood* 97, 3146-3151 (2001).
2. Cooper, M. A., Fehniger, T. A. & Caligiuri, M. A. The biology of human natural killer-cell subsets. *Trends Immunol* 22, 633-640 (2001).
3. Di Santo, J. P. Natural killer cells: diversity in search of a niche. Nat *Immunol* 9, 473-475 (2008).
4. Moretta, L. Dissecting CD56dim human NK cells. *Blood* 116, 3689-3691 (2010).
5. Romagnani, C. et al. CD56brightCD16—killer Ig-like receptor—NK cells display longer telomeres and acquire features of CD56dim NK cells upon activation. *J Immunol* 178, 4947-4955 (2007).
6. Berahovich, R D., Lai, N. L., Wei, Z., Lanier, L. L. & Schall, T. J. Evidence for NK cell subsets based on chemokine receptor expression. *J Immunol* 177, 7833-7840 (2006).
7. Robertson, M. J. Role of chemokines in the biology of natural killer cells. *J Leukoc Biol* 71, 173-183 (2002).
8. Trinchieri, G. & Gerosa, F. Immunoregulation by interleukin-12. J Leukoc Biol 59, 505-511 (1996).
9. McDyer, J. F., Wu, C. Y. & Seder, R. A. The regulation of IL-12: its role in infectious, autoimmune, and allergic diseases. *J Allergy Clin Immunol* 102, 11-15 (1998).
10. Loza, M. J. & Perussia, B. The IL-12 signature: NK cell terminal CD56+high stage and effector functions. JImmunol 172, 88-96 (2004).
11. Saez-Borderias, A. et al. IL-12-dependent inducible expression of the CD94/NKG2A inhibitory receptor regulates CD94/NKG2C+ NK cell function. *J Immunol* 182, 829-836 (2009).
12. Ljunggren, H. G. & Malmberg, K. J. Prospects for the use of NK cells in immunotherapy of human cancer. *Nat Rev Immunol* 7, 329-339 (2007).
13. Sutlu, T. & Alici, E. Natural killer cell-based immunotherapy in cancer: current insights and future prospects. *J Intern Med* 266, 154-181 (2009).
14. Spanholtz, J. et al. Clinical-grade generation of active NK cells from cord blood hematopoietic progenitor cells for immunotherapy using a closed-system culture process. *PLoS One* 6, e20740 (2011).
15. Spanholtz, J. et al. High log-scale expansion of functional human natural killer cells from umbilical cord blood CD34-positive cells for adoptive cancer immunotherapy. *PLoS One* 5, e9221 (2010).
16. Bennett, I. M. et al. Definition of a natural killer NKR-P1A+/CD56−/CD16− functionally immature human NK cell subset that differentiates in vitro in the presence of interleukin 12. J Exp Med 184, 1845-1856 (1996).
17. Guia, S. et al. A role for interleukin-12/23 in the maturation of human natural killer and CD56+ T cells in vivo. Blood 111, 5008-5016 (2008).
18. Galon, J., Sudarshan, C., Ito, S., Finbloom, D. & O'Shea, J. J. IL-12 induces IFN regulating factor-1 (IRF-1) gene expression in human NK and T cells. *J Immunol* 162, 7256-7262 (1999).
19. Yamamoto, K., Shibata, F., Miyasaka, N. & Miura, O. The human perforin gene is a direct target of STAT4 activated by IL-12 in NK cells. *Biochem Biophys Res Commun* 297, 1245-1252 (2002).
20. Zhang, C. C. & Lodish, H. F. Insulin-like growth factor 2 expressed in a novel fetal liver cell population is a growth factor for hematopoietic stem cells. *Blood* 103, 2513-2521 (2004).
21. Zhang, C. C. & Lodish, H. F. Murine hematopoietic stem cells change their surface phenotype during ex vivo expansion. *Blood* 105, 4314-4320 (2005).

22. Delaney, C. et al. Notch-mediated expansion of human cord blood progenitor cells capable of rapid myeloid reconstitution. *Nat Med* 16, 232-236 (2010).
23. Boitano, A. E. et al. Aryl hydrocarbon receptor antagonists promote the expansion of human hematopoietic stem cells. *Science* 329, 1345-1348 (2010).
24. Doulatov, S. et al. Revised map of the human progenitor hierarchy shows the origin of macrophages and dendritic cells in early lymphoid development. *Nat Immunol* 11, 585-593 (2010).
25. Grzywacz, B., Kataria, N., Blazar, B. R., Miller, J. S. & Verneris, M. R. Natural killer-cell differentiation by myeloid progenitors. *Blood* 117, 3548-3558 (2011).
26. Vacca, P. et al. CD34+ hematopoietic precursors are present in human decidua and differentiate into natural killer cells upon interaction with stromal cells. Proc Natl Acad Sci USA 108, 2402-2407 (2011).
27. Moroso, V. et al. NK cells can generate from precursors in the adult human liver. *Eur J Immunol* 41, 3340-3350 (2011).
28. Wojta, J., Hoover, R. L. & Daniel, T. O. Vascular origin determines plasminogen activator expression in human endothelial cells. Renal endothelial cells produce large amounts of single chain urokinase type plasminogen activator. *J Biol Chem* 264, 2846-2852 (1989).
29. Alter, G., Malenfant, J. M. & Altfeld, M. CD107a as a functional marker for the identification of natural killer cell activity. *J Immunol Methods* 294, 15-22 (2004).
30. Blomberg, K., Granberg, C., Hemmila, I. & Lovgren, T. Europium-labelled target cells in an assay of natural killer cell activity. I. A novel non-radioactive method based on time-resolved fluorescence. *J Immunol Methods* 86, 225-229 (1986).
31. Eissens, D. N. et al. Defining Early Human NK Cell Developmental
Stages in Primary and Secondary Lymphoid Tissues. *PLoS One* 7, e30930 (2012).
32. Takahashi, E. et al. Induction of CD16+ CD56bright NK cells with antitumour cytotoxicity not only from CD16– CD56bright NK Cells but also from CD16– CD56dim NK cells. *Scand J Immunol* 65, 126-138 (2007).
33. Beziat, V. et al. CD56brightCD16+ NK cells: a functional intermediate stage of NK cell differentiation. *J Immunol* 186, 6753-6761 (2011).
34. Juelke, K. et al. CD62L expression identifies a unique subset of polyfunctional CD56dim NK cells. *Blood* 116, 1299-1307 (2010). 35. Irjala, H. et al. Mannose receptor is a novel ligand for L-selectin and mediates lymphocyte binding to lymphatic endothelium. *J Exp Med* 194, 1033-1042 (2001).
36. Marttila-Ichihara, F. et al. Macrophage mannose receptor on lymphatics controls cell trafficking. *Blood* 112, 64-72 (2008).
37. Bhat, R. & Watzl, C. Serial killing of tumor cells by human natural killer cells-enhancement by therapeutic antibodies. *PLoS One* 2, e326 (2007).
38. Binyamin, L. et al. Blocking NK cell inhibitory self-recognition promotes antibody-dependent cellular cytotoxicity in a model of anti-lymphoma therapy. J Immunol 180, 6392-6401 (2008).

The invention claimed is:

1. A method for producing NK cells, said method comprising
   i. providing a sample of human CD34 positive cells,
   ii. expanding said CD34 positive cells ex vivo, and
   iii. culturing CD34 positive cells obtained in step ii ex vivo in an NK-cell differentiation medium such that NK cells are produced, said method characterized in that said NK-differentiation medium comprises a concentration of IL-12 that is between 0.2 ngram/ml and 20 ngram/ml.

2. A method according to claim 1, wherein said NK-differentiation medium comprises between 0.2 ngram/ml and 2 ngram/ml of IL-12.

3. A method according to claim 1, wherein step ii) is performed with a culture medium comprising three or more of stem cell factor (SCF), flt-3Ligand (FLT-3L), thrombopoietin (TPO) and interleukin-7 (IL-7) and three or more of granulocyte-macrophage-colony-stimulating factor (GM-CSF), granulocyte-colony-stimulating factor (G-CSF), interleukin-6 (IL-6), leukaemia-inhibitory factor (LIF) and Macrophage-inflammatory protein-lalpha (MIP-I alpha).

4. A method according to claim 1, wherein step iii) is performed with an NK-cell differentiation medium comprising one or more of IL-2 and IL-15; and one or more of IL-7 and SCF; and three or more GM-CSF, G-CSF, IL-6, LIF and MIP-I alpha.

5. A method according to claim 1, wherein step ii) is performed in culture medium comprising low molecular weight heparin.

* * * * *